United States Patent [19]
Hellring et al.

[11] Patent Number: 5,347,060
[45] Date of Patent: Sep. 13, 1994

[54] PHASE-TRANSFER CATALYSIS WITH ONIUM-CONTAINING SYNTHETIC MESOPOROUS CRYSTALLINE MATERIAL

[75] Inventors: Stuart D. Hellring, Yardley, Pa.; Jeffrey S. Beck, Princeton, N.J.

[73] Assignee: Mobil Oil Corporation, Fairfax, Va.

[21] Appl. No.: 75,010

[22] Filed: Jun. 11, 1993

Related U.S. Application Data

[63] Continuation of Ser. No. 735,238, Jul. 24, 1991, abandoned.

[51] Int. Cl.$^5$ .......................... C07C 17/20; B01J 31/18
[52] U.S. Cl. ..................... 570/235; 502/152; 502/164; 570/260
[58] Field of Search ................. 585/483, 486; 570/235, 570/260; 502/152, 164

[56] References Cited

U.S. PATENT DOCUMENTS

| | | | |
|---|---|---|---|
| 3,992,432 | 11/1976 | Napier et al. | 260/465 |
| 4,413,137 | 11/1983 | Renga et al. | 570/261 |
| 4,952,544 | 8/1990 | McCauley | 502/63 |
| 5,057,296 | 10/1991 | Beck | 423/277 |
| 5,099,054 | 3/1992 | Pinnavaia et al. | 585/436 |

OTHER PUBLICATIONS

Encyclopedia of Chemical Technology, vol. 5, J. Wiley & Sons, pp. 62–69.
"Ultralarge Pore Molecular Sieves", P. A. Jacobs & R. A. vanSanten, 1989 pp. 439–446.
P. Tundo et al, JCS Chem. Commun, p. 641 (1977).
P. Tundo et al, J. Amer. Chem. Soc., 104, 6551 (1982).

Primary Examiner—Asok Pal
Assistant Examiner—P. Achutamurtny
Attorney, Agent, or Firm—Alexander J. McKillop; Dennis P. Santini; Laurence P. Hobbes

[57] ABSTRACT

This invention relates to phase transfer catalysis (PTC) using a composition of synthetic ultra-large pore crystalline material which contains a cation of an onium compound, e.g. cetyltrimethylammonium, within the pores of said material. The crystalline material has, after calcination, an X-ray diffraction pattern with at least one peak at a d-spacing greater than 18 Angstrom Units and a benzene adsorption capacity of greater than 15 grams benzene per 100 grams of said material at 6.7 kPa (50 torr) and 25° C.

11 Claims, 22 Drawing Sheets

PHASE-TRANSFER CATALYSIS WITH ONIUM-CONTAINING SYNTHETIC MESOPOROUS CRYSTALLINE MATERIAL

This is a continuation of copending application Ser. No. 07/735,238, filed on Jul. 24, 1991, abandoned.

FIELD OF THE INVENTION

This invention relates to phase transfer catalysis (PTC) using a composition of synthetic ultra-large pore crystalline material which contains a cation of an onium compound, e.g. cetyltrimethylammonium, within the pores of said material.

BACKGROUND OF THE INVENTION

Phase-Transfer Catalysis

Phase-transfer catalysis (PTC) facilitates reactions between substances in different phases of a reaction medium. One or more of the reactants are organic liquids or solids dissolved in a water insoluble organic solvent and the coreactants are salts or alkali metal hydroxides in aqueous solution. In the absence of a phase-transfer catalyst the reactions are often slow or non-existent; in its presence the conversions occur rapidly and efficiently. Examples of such catalysts known in the art include onium compounds, e.g. quaternary ammonium or phosphonium salts, and crown ethers and cryptates. PTC is used for a wide variety of reactions including anion exchange; nucleophilic addition; nucleophilic substitution; reduction; alkylations of weak C-H acidic compounds up to a $pK_a$ limit of 22–25; alkylations of ambident anions; alkylations of OH, NH, and SH bonds; isomerizations and H-D-exchange; additions across C=C and C=O bonds; $\beta$-eliminations; formation of carbenes by $\alpha$-eliminations; hydrolysis and saponifications; Darzens reactions; Horner-Wittig reactions; oxidations, e.g. olefins to carboxylic acids; and reactions of sulfonium ylides.

Normally the above reactions are performed in homogenous media. However, the use of hydroxylic solvent alone results in the solvation of anion reactants which hinders the desired conversion reactions. Accordingly, expensive dipolar aprotic solvents are utilized to effect such reactions in a homogeneous environment. In contrast, carrying out these reactions by PTC avoids the need for such expensive solvents while simplifying workup, reducing reaction time and reaction temperatures. PTC is further advantageous in its use of aqueous alkali hydroxides as a substitute for more expensive bases. Additional information concerning PTC is found in Kirk-Othmer, Encyclopedia of Chemical Technology, Vol. 5, pp. 62 to 69, John Wiley & Sons, New York (1979), the contents of which are incorporated herein by reference.

Despite the advantages of PTC, common phase-transfer catalysts such as the onium compounds are soluble in water and thus difficult to reclaim from reaction media. To avoid such difficulties efforts have been made to provide phase transfer catalysts immobilized on a substrate. The use of such materials in PTC affords processing advantages such as simple filtration of the catalyst as well as its use in recycle and fixed bed applications. P. Tundo, et al., JCS Chem. Comm, p. 641 1977 discloses the immobilization of phase transfer catalysts on silica and alumina by reacting surface hydroxyls with Ω-bromoalkyltriethoxysilicates, e.g. $Br(CH_2)_3SiOCH_2CH_3$, then quaternizing with either tertiary phosphine or amines. P. Tundo, et al., J. Am. Chem. Soc. 1982 104, 6551 discloses a method which modifies silica and alumina by reacting surface hydroxyls with Ω-amino alkyltriethoxysilicates, e.g. $H_2N(CH_2)_3Si(OCH_2CH_3)_3$, followed by amidation with Ω-bromoalkylacid chlorides, then quaternizing with either tertiary phosphine or amines.

PTC using cetyltrimethylammonium is disclosed in U.S. Pat. No. 3,992,432, the entire contents of which being incorporated herein by reference.

Synthetic ultra-large pore non-layered crystalline materials can be prepared from a reaction mixture which utilizes onium compounds, e.g., cetyltrimethylammonium hydroxide, as a directing agent.

Applicants know of no prior art teaching the presently claimed use of synthetic ultra-large pore non-layered crystalline materials in phase-transfer catalysis.

SUMMARY OF THE INVENTION

The present invention is directed to a method for carrying out phase-transfer catalysis in a reaction system containing plural phases of varying polarity, e.g., an organic phase and an aqueous phase, using a phase-transfer catalyst containing a synthetic composition of matter comprising an ultra-large pore crystalline phase having immobilized quaternary onium ion within its pores. The crystalline phase material has, after calcination, an X-ray diffraction pattern with at least one peak at a d-spacing greater than 18 Angstrom Units and having a benzene adsorption capacity of greater than 15 grams benzene per 100 grams of said material at 6.7 kPa (50 torr) and 25° C.

The catalyst is prepared by crystallizing a porous metal oxide material around a directing agent which exhibits surfactant properties, e.g. cetyltrimethylammonium hydroxide. The catalyst so employed can be readily reclaimed from the reaction media, e.g. by filtration.

The method of the present invention can be used to catalyze nucleophilic substitution reactions, carbene formation, alkylations and alkoxylations, oxidations and reductions, and condensation, elimination, and addition reactions. More specifically, phase transfer catalysis can be used to catalyze the formation of ring compounds from straight-chain halocarbons, esters from acids, and ethers from alcohols; the synthesis of alkyl halides by anion displacement; the alkylation of carbanions; nucleophilic aromatic substitutions (as in the reaction of phenoxides with nitrophthalimides); and the oxidation of olefins to carboxylic acids and alcohols to carbonyls. Freedman, H. H. (Pure and Appl. Chem., 58 (1986), 857–868) sets forth a compilation of reaction types which are suited to practice by the present invention. Another suitable review of various topics and applications of phase transfer catalysis is given in ACS Symposium Series 326, C. M. Starks, ed. 1986, American Chemical Society, Washington. The term "phase transfer catalysis" is attributed to C. M. Starks (J. Am. Chem. Soc. 93, (1970), 195). The phase-transfer catalysis of the present invention is carried out under conditions which place the reactants the liquid state. Such conditions comprise pressures temperatures varying over a wide range. The normal temperature range will be 30° to 100° C. Sufficient pressure is utilized to maintain the system in the liquid state.

DESCRIPTION OF DRAWINGS

FIG. 19 is a transmission electron micrograph of the product of Example 4.

DESCRIPTION OF SPECIFIC EMBODIMENTS

Mesoporous Phase-Transfer Catalyst

Figure 1:
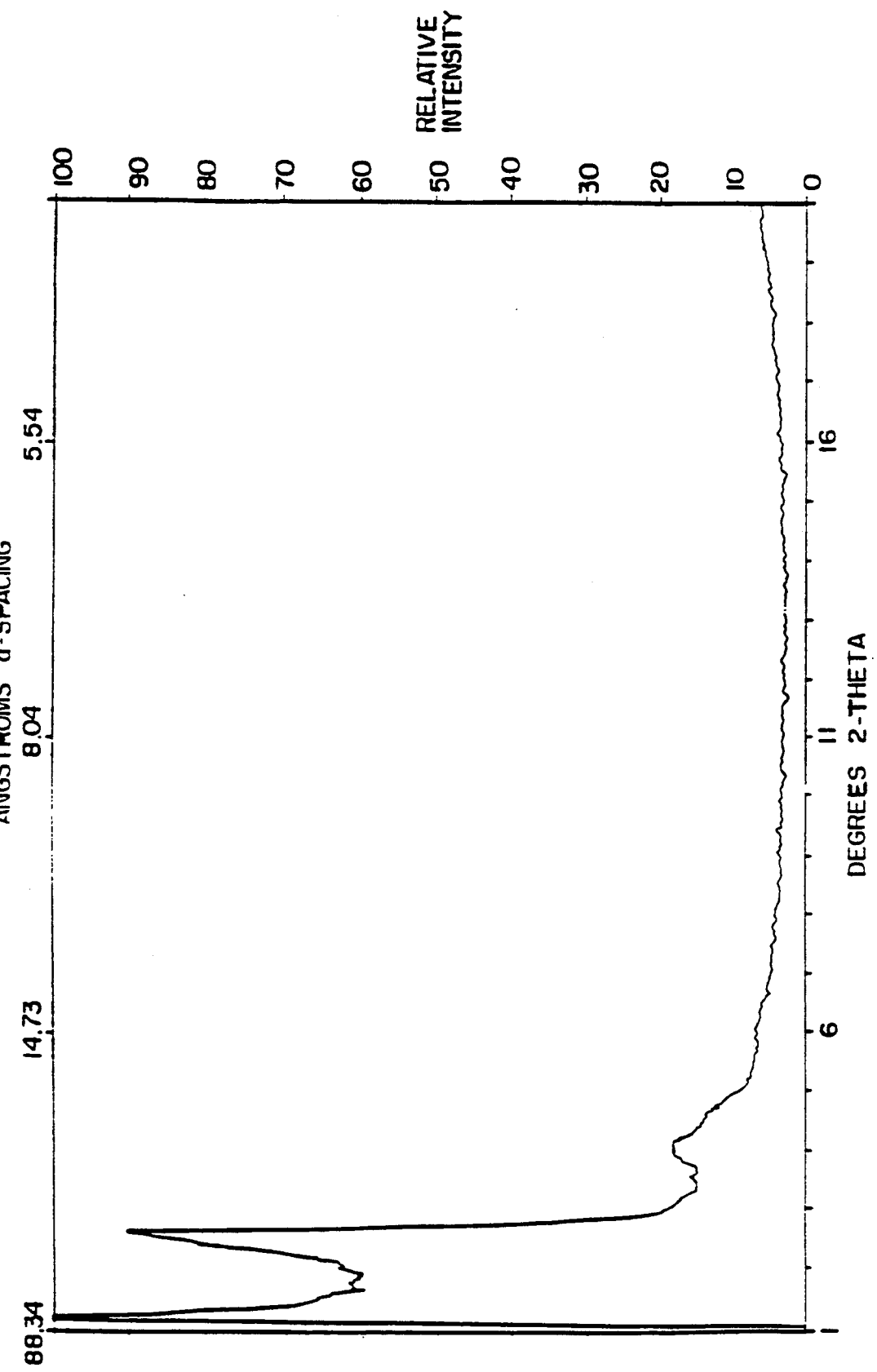
FIGS. 1–15 are X-ray diffraction patterns of products of Examples 1–14 and 16, respectively, hereinafter presented.

The present invention resides in the use of a mesoporous composition of matter containing onium ion within its pores as a phase-transfer catalyst. The catalyst transfers a functional reactant ion or group from one phase to another phase. The mesoporous composition of matter comprises an inorgamic, porous, non-layered crystalline phase material exhibiting, after calcination, an X-ray diffraction pattern with at least one peak, having a relative intensity of 100%, at a d-spacing greater than 1.8 nm and having a benzene adsorption capacity of greater than 15 grams benzene per 100 grams of said material at 6.7 kPa (50 torr) and 25° C.

In a preferred embodiment, the invention resides in the use of a composition of matter comprising an inorganic, porous crystalline phase material having a hexagonal arrangement of uniformly-sized pores at least 1.3 nm, preferably at least 1.5 nm, in diameter and exhibiting, after calcination, a hexagonal electron diffraction pattern that can be indexed with a $d_{100}$ value greater than 1.8 nm.

The pore sizes referred to herein are not strict crystallographic dimensions but instead are effective pore sizes determined by sorption measurement. The preferred method of determining pore size employs argon physisorption, which is a known technique and is described in detail in Examples 21(a) and 21 (b). In this method the mass of argon adsorbed by a sample at constant temperature but varying relative pressure above the sample is measured and used to plot an adsorption isotherm. The point on the isotherm corresponding to a rapid change of gradient indicates pore filling and can be used to determine pore size by the known mathematical relationships described in Example 21.

The crystalline (i.e. meant here as having sufficient order to provide, after calcination, a diffraction pattern with at least one peak by, for example, X-ray, electron or neutron diffraction) material used in this invention may be characterized by its structure, including extremely large pore windows, and high sorption capacity. In general, the material of the invention is "mesoporous" by which is meant that the material has uniform pores of diameter within the range of 1.3 to 20 nm. More preferably, the materials of the invention have uniform pores of diameter within the range 1.8 to 10 nm. In this respect, pore size is considered as the maximum perpendicular cross-sectional dimension of the pore.

The material used in the present invention can be distinguished from other porous inorganic solids by the regularity of its large open pores, whose size more nearly resembles that of amorphous or paracrystalline materials, but whose regular arrangement and uniformity of size (pore size distribution within a single phase of, for example, ±25%, usually ±15% or less of the average pore size of that phase) more closely resemble those of crystalline framework materials such as zeolites.

In the preferred arrangement, the porosity of the crystalline material used in the invention is provided by a generally hexagonal arrangement of open channels, a property that can be readily observed by electron diffraction and transmission electron microscopy. In particular, the transmission electron micrograph of properly oriented specimens of the material show a hexagonal arrangement of large channels and the corresponding electron diffraction pattern gives an approximately hexagonal arrangement of diffraction maxima. The $d_{100}$ spacing of the electron diffraction patterns is the distance between adjacent spots on the hk0 projection of the hexagonal lattice and is related to the repeat distance $a_0$ between channels observed in the electron micrographs through the formula $d_{100}=a_0\sqrt{3}/2$. This $d_{100}$ spacing observed in the electron diffraction patterns corresponds to the d-spacing of a low angle peak in the X-ray diffraction pattern of the material. The most highly ordered preparations of the material obtained so far have 20–40 distinct spots observable in the electron diffraction patterns. These patterns can be indexed with the hexagonal hk0 subset of unique reflections of 100, 110, 200, 210, etc., and their symmetry-related reflections.

In this respect, it is to be understood that the reference to a hexagonal arrangement of channels is intended to encompass not only mathematically perfect hexagonal symmetry but also an an arrangement in which most channels in the material are surrounded by six nearest neighbor channels at substantially the same distance. Defects and imperfections will cause significant numbers of channels to violate this criterion to varying degrees. Samples which exhibit as much as ±25% random deviation from the average repeat distance between adjacent channels still clearly give recognizable images of the present ultra-large pore materials.

The most regular preparations of the preferred material of the invention give a hexagonal X-ray diffraction pattern with a few distinct maxima in the extreme low angle region. The X-ray diffraction pattern, however, is not always a sufficient indicator of the presence of these materials, as the degree of regularity in the microstructure and the extent of repetition of the structure within individual particles affect the number of peaks that will be observed. Indeed, preparations with only one distinct peak in the low angle region of the X-ray diffraction pattern have been found to contain substantial amounts of the material of the invention.

In its calcined form, the crystalline material of the invention may be further characterized by an X-ray diffraction pattern with at least one peak at a position greater than about 1.8 nm d-spacing (4,909 degrees two-theta for Cu K-alpha radiation) which corresponds to the $d_{100}$ value of the electron diffraction pattern of the material.

More preferably, the calcined crystalline material of the invention is characterized by an X-ray diffraction pattern with at least two peaks at positions greater than about 1 nm d-spacing (8.842 degrees two-theta for Cu K-alpha radiation), at least one of which is at a position greater than 1.8 nm d-spacing, and no peaks at positions less than 1 nm d-spacing with relative intensity greater than about 20% of the strongest peak. Still more particularly, the X-ray diffraction pattern of the calcined material of this invention has no peaks at positions less than 1 nm d-spacing with relative intensity greater than about 10% of the strongest peak. In the preferred hexagonal arrangement, at least one peak in the X-ray pattern will have a d-spacing corresponding to the $d_{100}$ value of the electron diffraction pattern of the material.

X-ray diffraction data referred to herein were collected on a Scintag PAD X automated diffraction system employing theta-theta geometry, Cu K-alpha radiation, and an energy dispersive X-ray detector. Use of the energy dispersive X-ray detector eliminated the need for incident or diffracted beam monochromators. Both the incident and diffracted X-ray beams were collimated by double slit incident and diffracted collimation systems. The slit sizes used, starting from the X-ray tube source, were 0.5, 1.0, 0.3 and 0.2 mm, respectively. Different slit systems may produce differing intensities for the peaks. The materials of the present invention that have the largest pore sizes may require more highly collimated incident X-ray beams in order to resolve the low angle peak from the transmitted incident X-ray beam.

The diffraction data were recorded by step-scanning at 0.04 degrees of two-theta, where theta is the Bragg angle, and a relative intensities of the lines, $I/I_o$, where $I_o$ is counting time of 10 seconds for each step. The interplanar spacings, d's, were calculated in nanometers (nm), and the relative intensities of the lines, $I/I_o$, where $I_o$ is one-hundredth of the intensity of the strongest line, above background, were derived with the use of a profile fitting routine. The intensities were uncorrected for Lorentz and polarization effects. The relative intensities are given in terms of the symbols vs=very strong (75–100), s=strong (50–74), m=medium (25–49) and w=weak (0–24). It should be understood that diffraction data listed as single lines may consist of multiple overlapping lines which under certain conditions, such as very high experimental resolution or crystallographic changes, may appear as resolved or partially resolved lines. Typically, crystallographic changes can include minor changes in unit cell parameters and/or a change in crystal symmetry, without a substantial change in structure. These minor effects, including changes in relative intensities, can also occur as a result of differences in cation content, framework composition, nature and degree of pore filling, thermal and/or hydrothermal history, and peak width/shape variations due to particle size/shape effects, structural disorder or other factors known to those skilled in the art of X-ray diffraction.

The material used in the invention, after calcination, exhibits an equilibrium benzene adsorption capacity of greater than about 15 grams benzene/100 grams crystal at 6.7 kPa (50 torr) and 25° C. The equilibrium benzene adsorption capacity must, of course, be measured on a sample which exhibits no pore blockage by incidental contaminants. For example, water should be removed by dehydration techniques, e.g. thermal treatment, whereas inorganic amorphous materials, e.g. silica, and organics should be removed by contact with acid or base or other chemical agents and/or physical methods (such as, calcination) so that the detrital material is removed without detrimental effect on the material of the invention.

In general, crystalline material suited to use in this invention as a phase-transfer catalyst has the following composition:

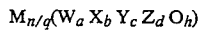
$$M_{n/q}(W_a X_b Y_c Z_d O_h)$$

wherein W is a divalent element, such as a divalent first row transition metal, e.g. manganese, cobalt, nickel, iron, and/or magnesium, preferably cobalt; X is a trivalent element, such as aluminum, boron, chromium iron and/or gallium, preferably aluminum; Y is a tetravalent element such as silicon and/or germanium, preferably silicon; Z is a pentavalent element, such as phosphorus; M is one or more ions, such as, for example, ammonium, Group IA, IIA and VIIB ions, usually hydrogen, sodium and/or fluoride ions; n is the charge of the composition excluding M expressed as oxides; q is the weighted molar average valence of M; n/q is the number of moles or mole fraction of M; a, b, c, and d are mole fractions of W, X, Y and Z, respectively; h is a number of from 1 to 2.5; and (a+b+c+d)=1. The material contains within its pores an onium ion, hereinafter described. The onium ion can be added to the composition during synthesis, or after synthesis by ion-exchange or impregnation techniques.

A preferred embodiment of the above crystalline material is when (a+b+c) is greater than d, and h=2. More preferably, when h=2, a=0 and d=0.

In the as-synthesized form, the material of this invention contains the onium ion immobilized within its pores, and has a composition, on an anhydrous basis, expressed empirically as follows:

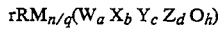
$$rRM_{n/q}(W_a X_b Y_c Z_d O_h)$$

wherein R is the total organic material used to assist in the synthesis of the material and not included in M as an ion, and r is the coefficient for R, i.e. the number of moles or mole fraction of R.

The M and R components are associated with the material as a result of their presence during crystallization, and are easily removed or, in the case of M, replaced by post-crystallization methods hereinafter more particularly described. For example, the original M, e.g. sodium or chloride, ions of the as-synthesized material of this invention can be replaced by ion exchange with other ions. Preferred replacing ions include metal ions, hydrogen ions, hydrogen precursor, e.g. ammonium, ions and mixtures thereof. Particularly preferred ions are those which tailor the catalytic activity for certain hydrocarbon conversion reactions. These include hydrogen, rare earth metals and metals of Groups IA (e.g. K), IIA (e.g. Ca), VIIA (e.g. Mn), VIIIA (e.g. Ni),IB (e.g. Cu), IIB (e.g. Zn), IIIB (e.g. In), IVB (e.g. Sn), and VIIB (e.g. F) of the Periodic Table of the Elements (Sargent-Welch Scientific Co. Cat. No. S-18806, 1979) and mixtures thereof.

Materials having the composition defined by the above formula can be prepared from a reaction mixture having a composition in terms of mole ratios of oxides, within the following ranges:

| Reactants | Useful | Preferred |
|---|---|---|
| $X_2O_3/YO_2$ | 0 to 0.5 | 0.001 to 0.5 |
| $X_2O_3/(YO_2 + Z_2O_5)$ | 0.1 to 100 | 0.1 to 20 |
| $X_2O_3/(YO_2 + WO + Z_2O_5)$ | 0.1 to 100 | 0.1 to 20 |
| Solvent/$(YO_2 + WO + Z_2O_5 + X_2O_3)$ | 1 to 1500 | 5 to 1000 |
| $OH^-/YO_2$ | 0 to 10 | 0 to 5 |
| $(M_{2/e}O + R_{2/f}O)/(YO_2 + WO + Z_2O_5 + X_2O_3)$ | 0.01 to 20 | 0.05 to 5 |
| $M_{2/e}O/(YO_2 + WO + Z_2O_5 + X_2O_3)$ | 0 to 10 | 0 to 5 |
| $R_{2/f}O/(YO_2 + WO + Z_2O_5 + X_2O_3)$ | 0.01 to 2.0 | 0.03 to 1.0 | wherein e and f are the weighted average valences of M and R, respectively, wherein the solvent is a $C_1$ to $C_6$ alcohol or diol, or, more preferably, water and wherein R comprises an organic directing agent comprising an onium ion having the formula $R_1R_2R_3R_4Q^+$ wherein Q is nitrogen or phosphorus and wherein at least one of $R_1$, $R_2$, $R_3$ and $R_4$ is aryl or alkyl group having 6 to 36 carbon atoms, e.g. $-C_{10}H_{21}$, $-C_{16}H_{33}$ and $-C_{18}H_{37}$, and each of the remainder of $R_1$, $R_2$, $R_3$ and $R_4$ is selected from hydrogen and an alkyl group having 1 to 5 carbon atoms. The compound from which the above ammonium or phosphonium ion is derived may be, for example, the hydroxide, halide, silicate or mixtures thereof.

The particular effectiveness of the above directing agent, when compared with other such agents known to direct synthesis of one or more other crystal structures, is believed due to its ability to function as a template in the nucleation and growth of the desired ultra-large pore materials. Non-limiting examples of these directing agents include cetyltrimethylammonium, cetyltrimethylphosphonium, octadecyltrimethylphosphonium, cetylpyridinium, myristyltrimethylammonium, decyltrimethylammonium, dodecyltrimethylammonium and dimethyldidodecylammonium compounds.

Preferably, the total organic, R, present in the reaction mixture comprises an additional organic directing agent in the form of an ammonium or phosphonium ion of the above directing agent formula but wherein each $R_1$, $R_2$, $R_3$ and $R_4$ is selected from hydrogen and an alkyl group of 1 to 5 carbon atoms (2 of the alkyl groups can be interconnected to form a cyclic compound). Examples of the additional organic directing agent include tetramethylammonium, tetraethylammonium, tetrapropylammonium, tetrabutylammonium and pyrrolidinium compounds. The molar ratio of the first-mentioned organic directing agent to the additional organic directing agent can be in the range 100/1 to 0.01/1. Where the additional organic directing agent is present, the molar ratio $R_{2/f}O/(YO_2+WO+Z_2O_5+X_2O_3)$ in the reaction mixture is preferably 0.1 to 2.0, most preferably 0.12 to 1.0.

In an even more preferred embodiment of the invention the mesoporous crystalline material is prepared by a method which permits varying the pore size of the final crystalline phase material. The total organic, R, in the reaction mixture can include an auxiliary organic in addition to the organic directing agent(s) described above. This auxiliary organic is selected from (1) aromatic hydrocarbons and amines having 5-20 carbon atoms and halogen- and $C_1-C_{14}$ alkyl-substituted derivatives thereof, (2) cyclic and polycyclic aliphatic hydrocarbons and amines of 5 to 20 carbon atoms and halogen- and $C_1-C_{14}$ alkyl-substituted derivatives thereof and (3) straight and branched chain aliphatic hydrocarbons and amines having 3-16 carbon atoms and halogen-substituted derivatives thereof.

In the above auxiliary organics, the halogen substituent is preferably bromine. The $C_1-C_{14}$ alkyl substituent may be a linear or branched aliphatic chain, such as, for example, methyl, ethyl, propyl, isopropyl, butyl, pentyl and combinations thereof. Examples of these auxiliary organics include, for example, p-xylene, trimethylbenzene, triethylbenzene and triisopropylbenzene. Of these, trimethylbenzene, i.e., mesitylene, is especially preferred.

With the inclusion of the auxiliary organic in the reaction mixture, the mole ratio of auxiliary organic/$YO_2$ will be from 0.05 to 20, preferably from 0.1 to 10, and the mole ratio of auxiliary organic/organic directing agent(s) will be from 0.02 to 100, preferably from 0.05 to 35.

When a source of silicon is used in the synthesis method, it is preferred to use at least in part an organic silicate, such as, for example, a quaternary ammonium silicate. Non-limiting examples of such a silicate include tetramethylammonium silicate and tetraethylorthosilicate.

Non-limiting examples of various combinations of W, X, Y and Z contemplated for the above reaction mixture include:

| W | X | Y | Z |
|---|---|---|---|
| — | Al | Si | — |
| — | Al | — | P |
| — | Al | Si | P |
| Co | Al | — | P |
| Co | Al | Si | P |
| — | — | Si | — | including the combinations of W being Mg, or an element selected from the divalent first row transition metals, e.g. Mn, Co and Fe; X being B, Ga or Fe; and Y being Ge.

To produce the crystalline material used in the invention, the reaction mixture described above is maintained at a temperature of 25° to 250° C., preferably 50° to 175° C., and preferably a pH of 9 to 14 for a period of time until the required crystals form, typically 5 minutes to 14 days, more preferably 1 to 300 hours.

When the crystalline material of the invention is an aluminosilicate, the synthesis method conveniently involves the following steps:

(1) Mix the organic (R) directing agent with the solvent or solvent mixture such that the mole ratio of solvent/$R_{2/f}O$ is within the range of 50 to 800, preferably from 50 to 500. This mixture constitutes the "primary template" for the synthesis method.

(2) To the primary template mixture of step (1) add the silica and alumina such that the ratio of $R_{2/f}O/(SiO_2+Al_2O_3)$ is within the range 0.01 to 2.0.

(3) Agitate the mixture resulting from step (2) at a temperature of 20° to 40° C., preferably for 5 minutes to 3 hours.

(4) Allow the mixture to stand with or without agitation, preferably at 20° to 50° C., and preferably for 10 minutes to 24 hours.

(5) Crystallize the product from step (4) at a temperature of 50° to 150° C., preferably for 1 to 72 hours.

Although such mesoporous compositions are usually subjected to treatment to remove part or all of any organic constituent when used as a sorbent or catalyst component, it is desirable in the present invention to utilize the onium ion present in the as-synthesized materials as the onium ion needed for the phase-transfer catalyst. Accordingly, precautions should be taken to avoid subjecting the as-synthesized materials to conditions which would remove onium ion from the pores of the mesoporous crystalline material, e.g. temperatures above 540° C. Nevertheless, the as-synthesized material can be subjected to conditions which wash off onium ion from the surface of the material in the course of catalyst work-up.

The mesoporous composition used in the present invention can contain a hydrogenating component such as tungsten, vanadium, molybdenum, rhenium, nickel, cobalt, chromium, manganese, or a noble metal such as platinum or palladium or mixtures thereof where a hydrogenation-dehydrogenation function is to be performed. Such component can be in the composition by way of co-crystallization, exchanged into the composition to the extent a Group IIIB element, e.g. aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above crystalline material, especially in its metal, hydrogen and ammonium forms can be beneficially converted to another form by thermal treatment (calcination). This thermal treatment is generally performed at a temperature of 400° to 750° C. for at least 1 minute and generally not longer than 20 hours, preferably from 1 to 10 hours. While subatmospheric pressure can be employed for the thermal treatment, atmospheric pressure is desired for reasons of convenience, such as in air, nitrogen and ammonia. The thermally treated product is particularly useful in the catalysis of certain hydrocarbon conversion reactions. However, for purposes of the present invention, the onium ion content lost by such thermal treatment must be restored by any suitable means, e.g., ion-ixchange or impregnation, to levels affording phase-transfer catalyst behavior.

The mesoporous crystalline material used in this invention, when employed either as an adsorbent or as a catalyst component in an organic compound conversion process should be dehydrated, at least partially. This can be done by heating to a temperature in the range of 200° C. to 595° C. in an atmosphere such as air, nitrogen, etc. and at atmospheric, subatmospheric or superatmospheric pressures for between 30 minutes and 48 hours. Dehydration can also be performed at room temperature merely by placing the composition in a vacuum, but a longer time is required to obtain a sufficient amount of dehydration.

The present compositions are useful as catalyst components for catalyzing the conversion of organic compounds, e.g. oxygenates and hydrocarbons, by acid-catalyzed reactions. The size of the pores is such that the spatiospecific selectivity with respect to transition state species is minimized in reactions such as cracking (see Chen et al., "Shape Selective Catalysis in Industrial Applications", 36 CHEMICAL INDUSTRIES, pgs. 41-61 (1989)). Diffusional limitations are also minimized as a result of the very large pores in the present materials. For these reasons, the present compositions are especially useful for catalyzing reactions which occur in the presence of acidic sites on the surface of the catalyst and which involve reactants, products or transitional state species which have large molecular sizes. The use of mesoporous crystalline materials in phase transfer catalysis can impart shape-selectivity to the reactions thus practiced where reactions involve organic molecules of sufficient kinetic diameter to be constrained by pore diameter.

Thus, the present catalytic compositions are particularly useful in the conversion of organic compounds of large molecular size such as highly aromatic hydrocarbons with substituted or unsubstituted polycyclic aromatic components, bulky naphthenic compounds or highly substituted compounds with bulky steric configurations, e.g. molecular sizes of 1.3 nm or more.

As in the case of many catalysts, it may be desired to incorporate the new crystal composition with another material resistant to the temperatures and other conditions employed in organic conversion processes. Such materials include active and inactive materials and synthetic or naturally occurring zeolites as well as inorganic materials such as clays, silica and/or metal oxides such as alumina, titania and/or zirconia. The latter may be either naturally occurring or in the form of gelatinous precipitates or gels including mixtures of silica and metal oxides. Use of a material in conjunction with the new crystal, i.e. combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated with naturally occurring clays, e.g. bentonite and kaolin, to improve the crush strength of the catalyst under commercial operating conditions. Said materials, i.e. clays, oxides, etc., function as binders for the catalyst. It is desirable to provide a catalyst having good crush strength because in commercial use it is desirable to prevent the catalyst from breaking down into powder-like materials. These clay binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

It may be desirable to provide at least a part of the foregoing matrix materials in colloidal form so as to facilitate extrusion of the bound catalyst component(s).

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented. In the examples, whenever sorption data are set forth for comparison of sorptive capacities for water, cyclohexane, benzene and/or n-hexane, they are Equilibrium Adsorption values determined as follows:

A weighed sample of the adsorbent, after calcination at about 540° C. for at least about 1 hour and other treatment, if necessary, to remove any pore blocking contaminants, is contacted with the desired pure adsorbate vapor in an adsorption chamber. The increase in weight of the adsorbent is calculated as the adsorption capacity of the sample in terms of grams/100 grams adsorbent based on adsorbent weight after calcination at about 540° C. The present composition exhibits an equilibrium benzene adsorption capacity at 50 Torr and 25° C. of greater than about 15 grams/100 grams, particularly greater than about 17.5 g/100 g/ and more particularly greater than about 20 g/100 g.

A preferred way to do this is to contact the desired pure adsorbate vapor in an adsorption chamber evacuated to less than 1 mm at conditions of 12 Torr of water vapor, 40 Torr of n-hexane or cyclohexane vapor, or 50 Torr of benzene vapor, at 25° C. The pressure is kept constant (within about ±0.5 mm) by addition of adsorbate vapor controlled by a manostat during the adsorption period. As adsorbate is adsorbed by the new crystal, the decrease in pressure causes the manostat to open a valve which admits more adsorbate vapor to the chamber to restore the above control pressures. Sorption is complete when the pressure change is not sufficient to activate the manostat.

Another way of doing this for benzene adsorption data is on a suitable thermogravimetric analysis system, such as a computer-controlled 990/951 dupont TGA system. The adsorbent sample is dehydrated (physically sorbed water removed) by heating at, for example, about 350° C. or 500° C. to constant weight in flowing helium. If the sample is in as-synthesized form, e.g. containing organic directing agents, it is calcined at about 540° C. in air and held to constant weight instead of the previously described 350° C. or 500° C. treatment. Benzene adsorption isotherms are measured at 25° C. by blending a benzene saturated helium gas stream with a pure helium gas stream in the proper proportions to obtain the desired benzene partial pressure. The value of the adsorption at 50 Torr of benzene is taken from a plot of the adsorption isotherm.

In the examples, percentages are by weight unless otherwise indicated.

EXAMPLE 1

One hundred grams of cetyltrimethylammonium (CTMA) hydroxide solution, prepared by contacting a 29 wt. % N,N,N-trimethyl-1-hexadecanaminium chloride solution with a hydroxide-for-halide exchange resin, was combined with 100 grams of an aqueous solution of tetramethylammonium (TMA) silicate (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a polypropylene bottle, which was kept in a steam box at 95° C. overnight. The mixture had a composition in terms of moles per mole $Al_2O_3$:

| |
|---|
| 2.7 moles $Na_2O$ |
| 392 moles $SiO_2$ |
| 35.7 moles $(CTMA)_2O$ |
| 61.7 moles $(TMA)_2O$ |
| 6231 moles $H_2O$ |

The resulting solid product was recovered by filtration and dried in air at ambient temperature. The product was then calcined at 540° C. for 1 hour in nitrogen, followed by 6 hours in air.

The calcined product proved to have a surface area of 475 $m^2$/g and the following equilibrium adsorption capacities in grams/100 grams:

| | |
|---|---|
| $H_2O$ | 8.3 |
| Cyclohexane | 22.9 |
| n-Hexane | 18.2 |
| Benzene | 21.5 |

The X-ray diffraction pattern of the calcined product of this example is shown in FIG. 1. In this and the following Figures, it is noted that 10 Angstrom Units d-spacing corresponds to 8.842 degrees 2-theta (Cu K-alpha radiation) and 18 Angstrom Units corresponds to 4.909 degrees.

The product of this example may be characterized as including a very strong relative intensity line at 37.8±2.0 Angstroms d-spacing, and weak lines at 21.6±1.0 and 19.2±1.0 Angstroms. The present ultra-large pore material was demonstrated to be in the product of this example by transmission electron microscopy (TEM), which produced images of a hexagonal arrangement of uniform pores and hexagonal electron diffraction pattern with a $d_{100}$ value of about 39 Angstroms.

EXAMPLE 2

One hundred grams of cetyltrimethylammonium (CTMA) hydroxide solution prepared as in Example 1 was combined with 100 grams of an aqueous solution of tetramethylammonium (TMA) hydroxide (25%) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. overnight. The mixture had a composition in terms of moles per mole $Al_2O_3$:

| |
|---|
| 2.7 moles $Na_2O$ |
| 291 moles $SiO_2$ |
| 35.7 moles $(CTMA)_2O$ |
| 102 moles $(TMA)_2O$ |
| 6120 moles $H_2O$ |

The resulting solid product was recovered by filtration and dried in air at ambient temperature. The product was then calcined at 540° C. for 1 hour in nitrogen, followed by 6 hours in air.

The calcined product proved to have a surface area of 993 $m^2$/g and the following equilibrium adsorption capacities in grams/100 grams:

| | |
|---|---|
| H₂O | 7.1 |
| Cyclohexane | 47.2 |
| n-Hexane | 36.2 |
| Benzene | 49.5 |

Figure 2:
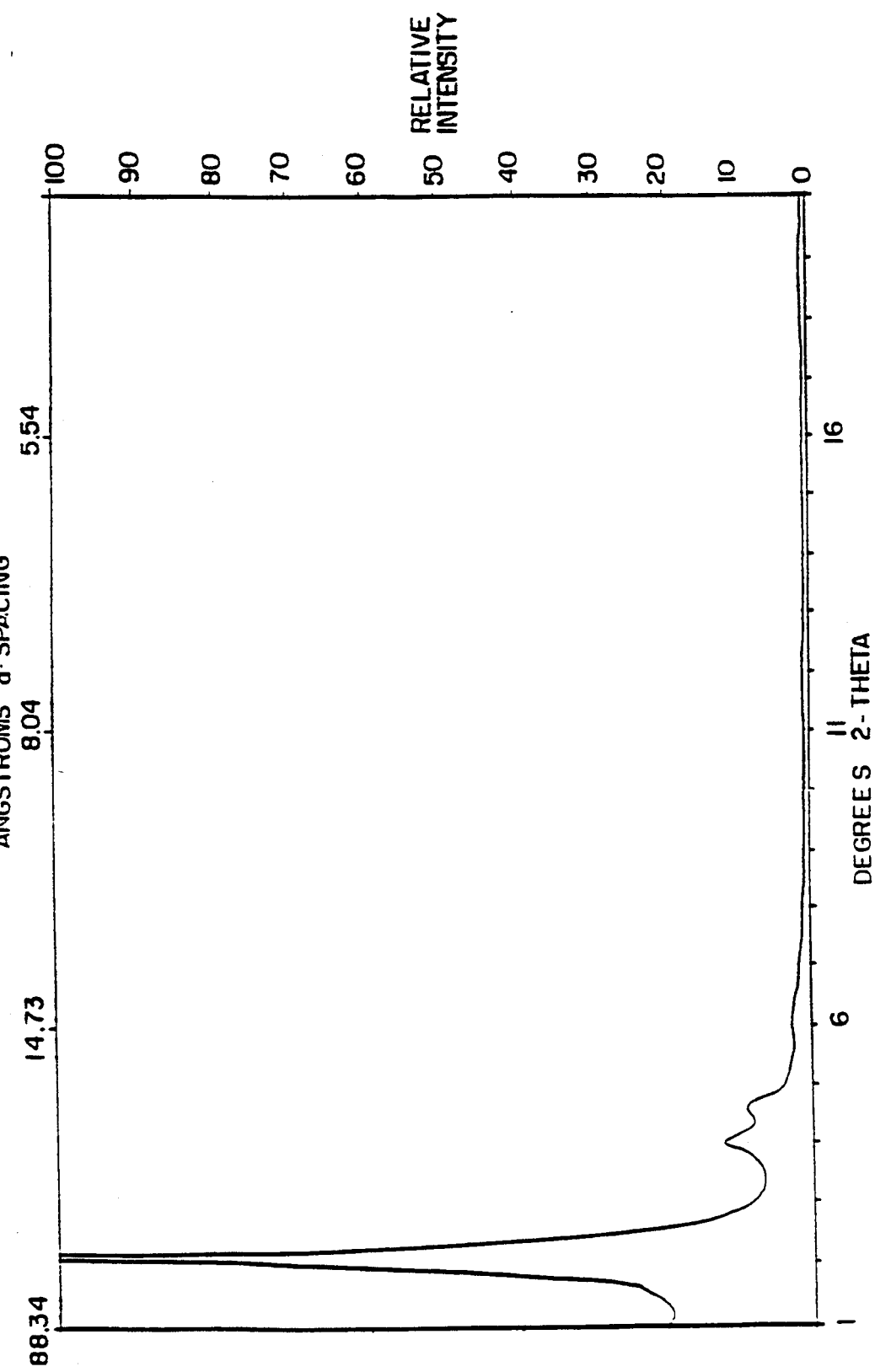

The X-ray diffraction pattern of the calcined product of this example is shown in FIG. 2. It may be characterized as including a very strong relative intensity line at 39.3±2.0 Angstroms d-spacing, and weak lines at 22.2±1.0 and 19.4±1.0 Angstroms. TEM indicated that the product contained the present ultra-large pore material.

A portion of the above product was then contacted with 100% steam at 1450° F. for two hours. The surface area of the steamed material was measured to be 440 m²/g, indicating that about 45% was retained following severe steaming.

Another portion of the calcined product of this example was contacted with 100% steam at 1250° F. for two hours. The surface area of this material was measured to be 718 m²/g, indicating that 72% was retained after steaming at these conditions.

EXAMPLE 3

Water, cetyltrimethylammonium hydroxide solution prepared as in Example 1, aluminum sulfate, HiSil and an aqueous solution of tetrapropylammonium (TPA) bromide (35%) were combined to produce a mixture having a composition in terms of moles per mole Al₂O₃:

| |
|---|
| 0.65 moles Na₂O |
| 65 moles SiO₂ |
| 8.8 moles (CTMA)₂O |
| 1.22 moles (TPA)₂O |
| 1336 moles H₂O |

The resulting mixture was placed in a polypropylene bottle, which was kept in a steam box at 95° C. for 192 hours. The sample was then cooled to room temperature and combined with CTMA hydroxide solution prepared as in Example 1 and TMA hydroxide (25% by weight) in the weight ratio of 3 parts mixture, 1 part CTMA hydroxide and 2 parts TMA hydroxide. The combined mixture was then placed in a polypropylene bottle and kept in a steam box at 95° C. overnight. The combined mixture had a composition in terms of moles per mole Al₂O₃:

| |
|---|
| 0.65 moles Na₂O |
| 65 moles SiO₂ |
| 15 moles (CTMA)₂O |
| 1.22 moles (TPA)₂O |
| 35.6 moles (TMA)₂O |
| 2927 moles H₂O |

The resulting solid product was recovered by filtration and dried in air at ambient temperature. The product was then calcined at 540° C. for 1 hour in nitrogen, followed by 6 hours in air.

The calcined product proved to have a surface area of 1085 m²/g and the following equilibrium adsorption capacities in grams/100 grams:

| | |
|---|---|
| H₂O | 11.5 |

-continued

| | |
|---|---|
| Cyclohexane | >50 |
| n-Hexane | 39.8 |
| Benzene | 62 |

Figure 3:
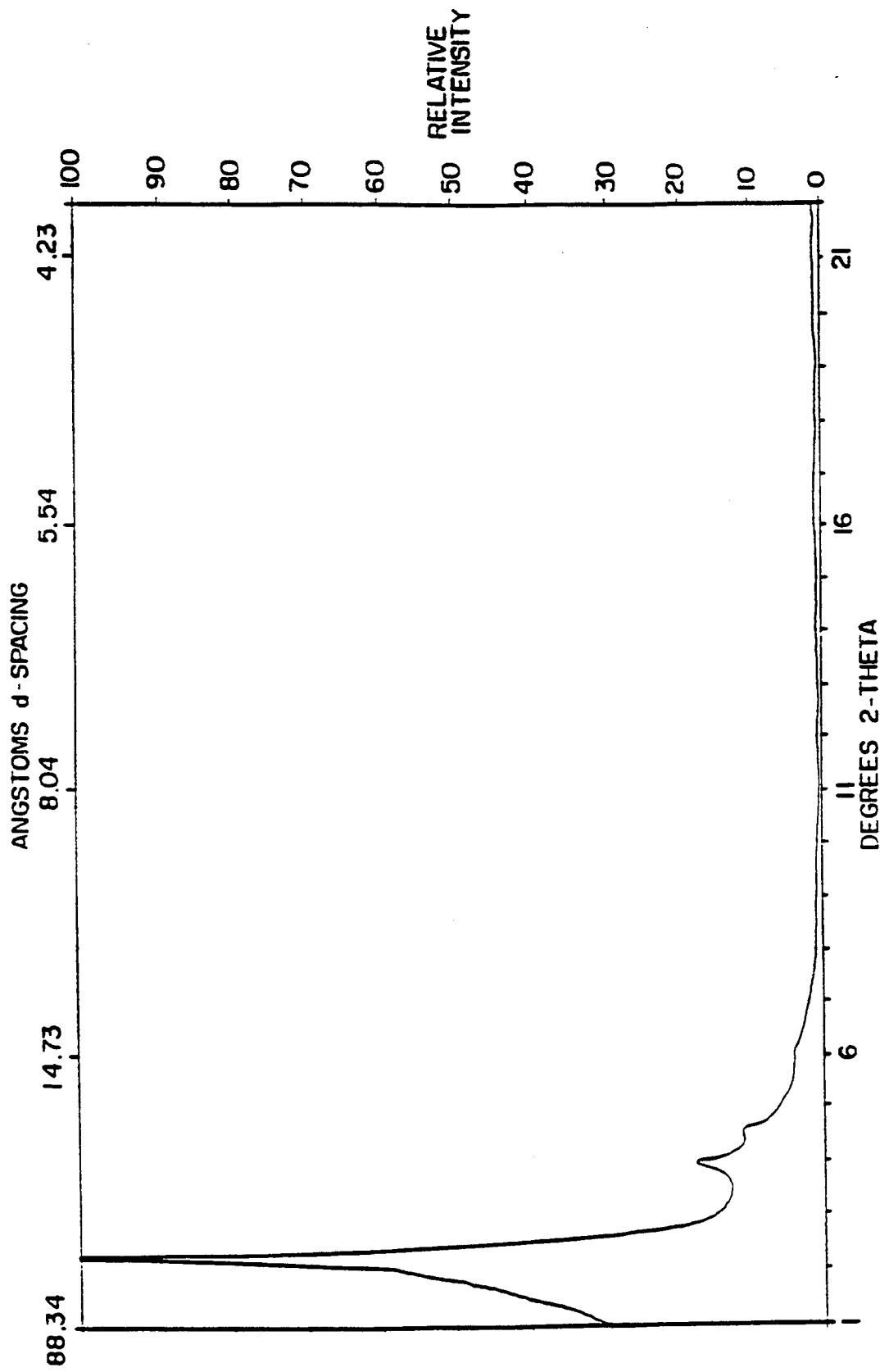

The X-ray diffraction pattern of the calcined product of this example is shown in FIG. 3. The product of this example may be characterized as including a very strong relative intensity line at 38.2±2.0 Angstroms d-spacing, and weak lines at 22.2±1.0 and 19.4±1.0 Angstroms. TEM indicated the product contained the present ultra-large pore material.

EXAMPLE 4

Two hundred grams of cetyltrimethylammonium (CTMA) hydroxide solution prepared as in Example 1 was combined with 2 grams of Catapal alumina (alpha-alumina monohydrate, 74% alumina) and 100 grams of an aqueous solution of tetramethylammonium (TMA) silicate (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. for 48 hours. The mixture had a composition in terms of moles per mole Al₂O₃:

| |
|---|
| 0.23 moles Na₂O |
| 33.2 moles SiO₂ |
| 6.1 moles (CTMA)₂O |
| 5.2 moles (TMA)₂O |
| 780 moles H₂O |

The resulting solid product was recovered by filtration and dried in air at ambient temperature. The product was then calcined at 540° C. for 1 hour in nitrogen, followed by 6 hours in air.

The calcined product proved to have a surface area of 1043 m²/g and the following equilibrium adsorption capacities in grams/100 grams:

| | |
|---|---|
| H₂O | 6.3 |
| Cyclohexane | >50 |
| n-Hexane | 49.1 |
| Benzene | 66.7 |

Figure 4:
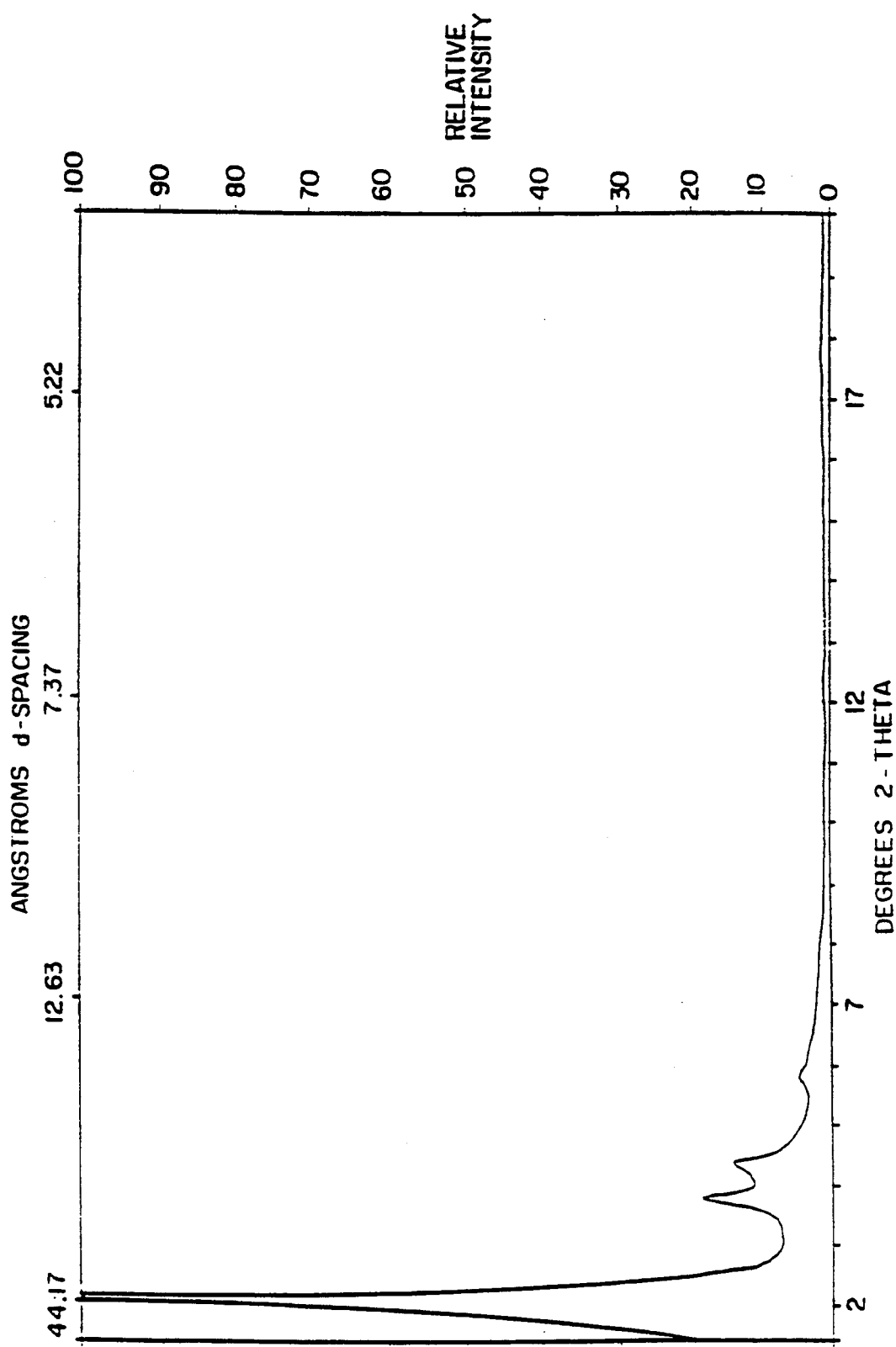

The X-ray diffraction pattern of the calcined product of this example is shown in FIG. 4. It may be characterized as including a very strong relative intensity line at 40.8±2.0 Angstroms d-spacing, and weak lines at 23.1±1.0 and 20.1± 1.0 Angstroms. TEM indicated that the product contained the present ultra-large pore material (see Example 23).

EXAMPLE 5

Two-hundred sixty grams of water was combined with 77 grams of phosphoric acid (85%), 46 grams of Catapal alumina (74% alumina), and 24 grams of pyrrolidine (Pyr) with stirring. This first mixture was placed in a stirred autoclave and heated to 150° C. for six days. The material was filtered, washed and air-dried. Fifty grams of this product was slurried with 200 grams of water and 200 grams of cetyltrimethylammonium hydroxide solution prepared as in Example 1. Four hundred grams of an aqueous solution of tetraethylammonium silicate (10% silica) was then added to form a second mixture which was placed in a polypropylene bottle and kept in a steam box at 95° C. overnight. The first mixture had a composition in terms of moles per mole $Al_2O_3$:

| |
|---|
| 1.0 moles $P_2O_5$ |
| 0.51 moles $(Pyr)_2O$ |
| 47.2 moles $H_2O$ |

The resulting solid product was recovered by filtration and dried in air at ambient temperature. The product was then calcined at 540° C. for 1 hour in nitrogen, followed by 6 hours in air.

The calcined product proved to have a surface area of 707 m²/g and the following equilibrium adsorption capacities in grams/100 grams:

| | |
|---|---|
| Cyclohexane | 19.7 |
| n-Hexane | 20.1 |
| Benzene | 23.3 |

Figure 5:
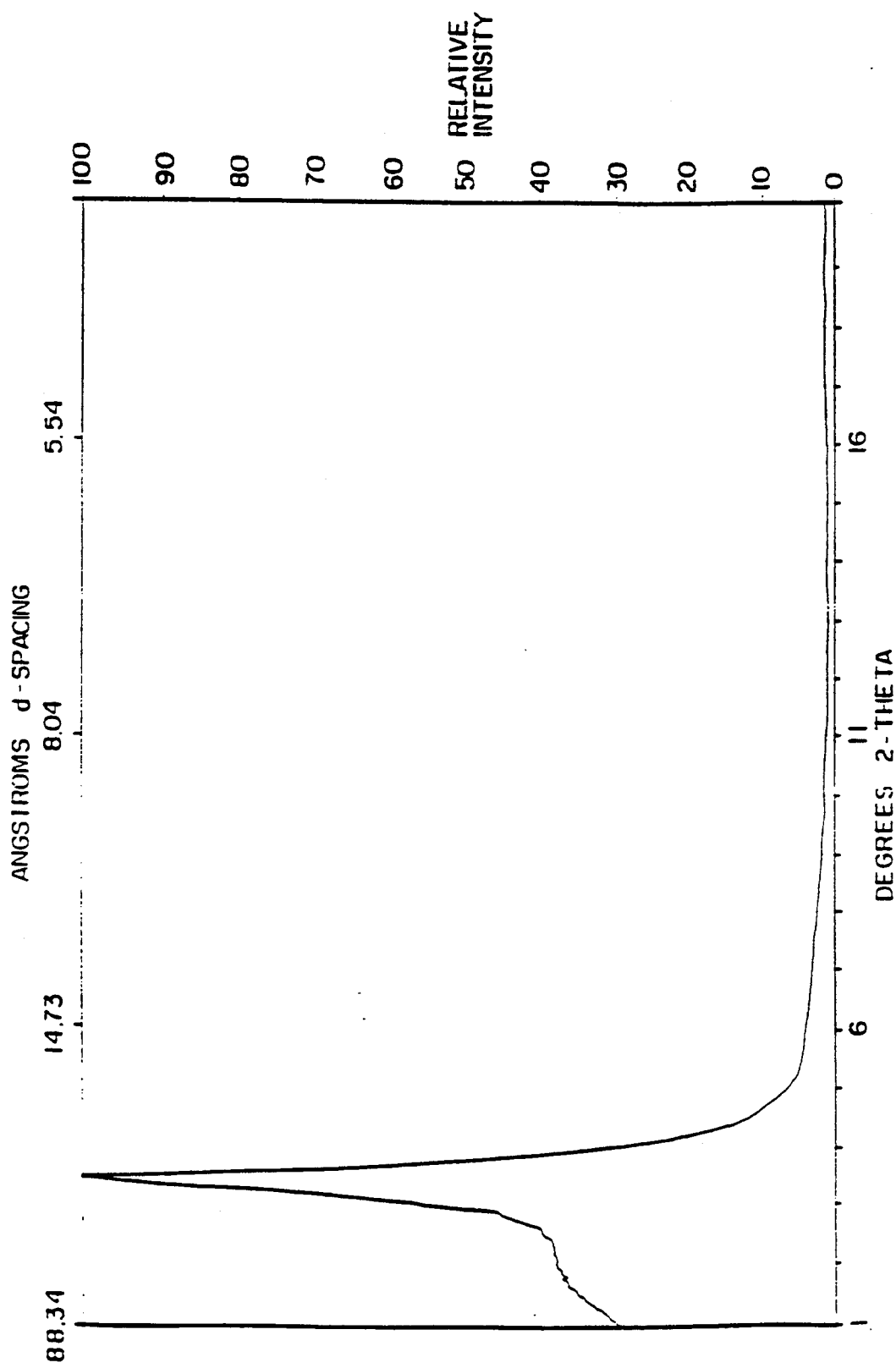

The X-ray diffraction pattern of the calcined product of this example is shown in FIG. 5. It may be characterized as including a very strong relative intensity line at 25.4±1.5 Angstroms d-spacing. TEM indicated the product contained the present ultra-large pore material (see Example 23).

EXAMPLE 6

A solution of 1.35 grams of $NaAlO_2$ (43.5% $Al_2O_3$, 30% $Na_2O$) dissolved in 45.2 grams of water was mixed with 17.3 grams of NaOH, 125.3 grams of colloidal silica (40%, Ludox HS-40) and 42.6 grams of 40% aqueous solution of tetraethylammonium (TEA) hydroxide. After stirring overnight, the mixture was heated for 7 days in a steam box (95° C.). Following filtration, 151 grams of this solution was mixed with 31 grams of cetyltrimethylammonium hydroxide solution prepared as in Example 1 and stored in the steam box at 95° C. for 13 days. The mixture had the following relative molar composition:

| |
|---|
| 0.25 moles $Al_2O_3$ |
| 10 moles $Na_2O$ |
| 36 moles $SiO_2$ |
| 0.95 moles $(CTMA)_2O$ |
| 2.5 moles $(TEA)_2O$ |
| 445 moles $H_2O$ |

The resulting solid product was recovered by filtration and washed with water and ethanol. The product was then calcined at 540° C. for 1 hour in nitrogen, followed by 6 hours in air.

The calcined product composition included 0.14 wt. % Na, 68.5 wt. % $SiO_2$ and 5.1 wt. % $Al_2O_3$, and proved to have a benzene equilibrium adsorption capacity of 58.6 grams/100 grams.

Figure 6:
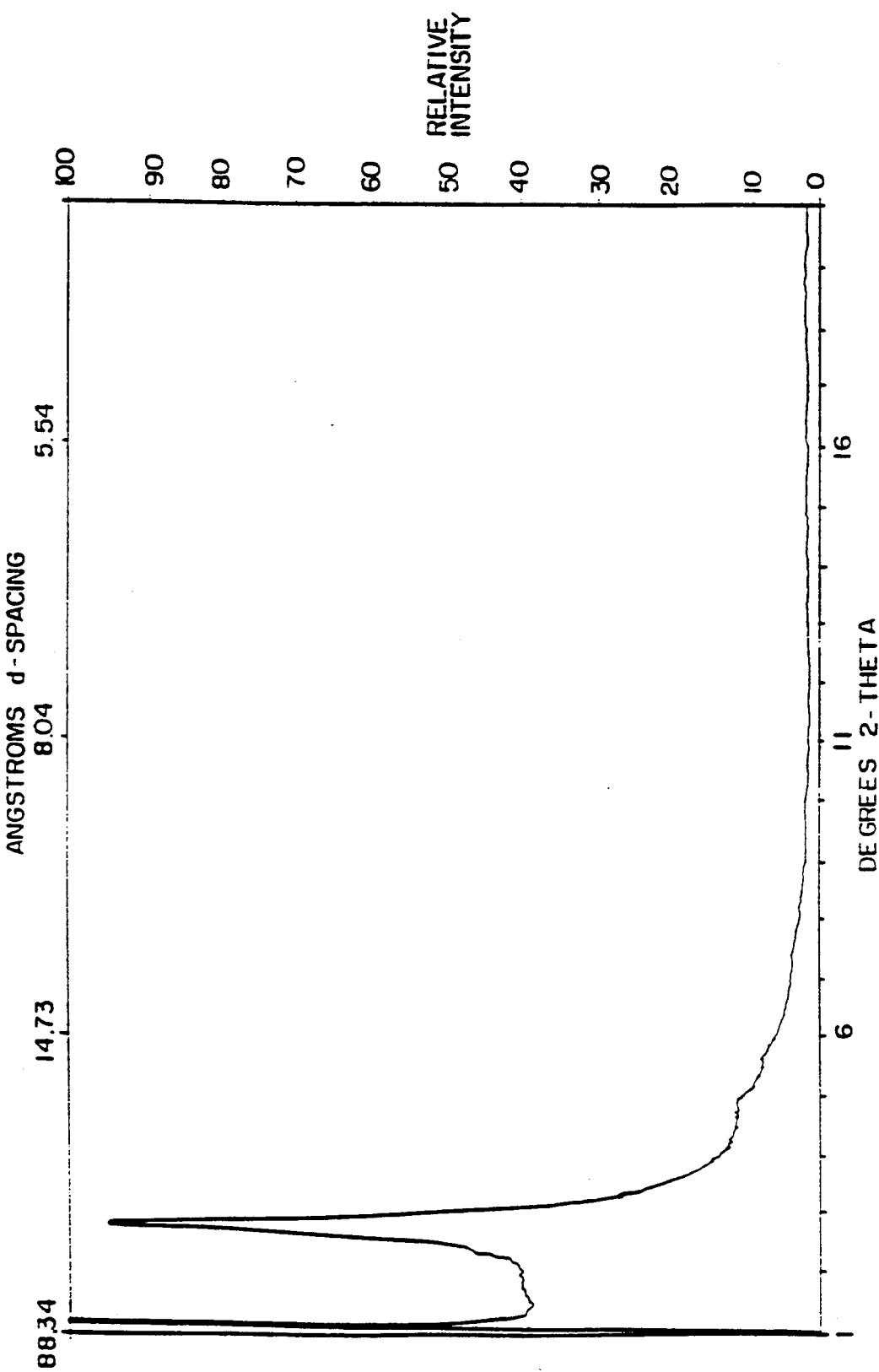

The X-ray diffraction pattern of the calcined product of this example is shown in FIG. 6. The product of this example may be characterized as including a very strong relative intensity line at 31.4±1.5 Angstroms d-spacing. TEM indicated that the product contained the present ultra-large pore material.

EXAMPLE 7

A mixture of 300 grams of cetyltrimethylammonium (CTMA) hydroxide solution prepared as in Example 1 and 41 grams of colloidal silica (40%, Ludox HS-40) was heated in a 600 cc autoclave at 150° C. for 48 hours with stirring at 200 rpm. The mixture has a composition in terms of moles per mole $SiO_2$:

The resulting solid product was recovered by filtration, washed with water, then calcined at 540° C. for 1 hour in nitrogen, followed by 10 hours in air.

The calcined product composition included less than 0.01 wt. % Na, about 98.7 wt. % $SiO_2$ and about 0.01 wt. % $Al_2O_3$, and proved to have a surface area of 896 m²/g. The calcined product had the following equilibrium adsorption capacities in grams/100 grams:

| | |
|---|---|
| $H_2O$ | 8.4 |
| Cyclohexane | 49.8 |
| n-Hexane | 42.3 |
| Benzene | 55.7 |

Figure 7:
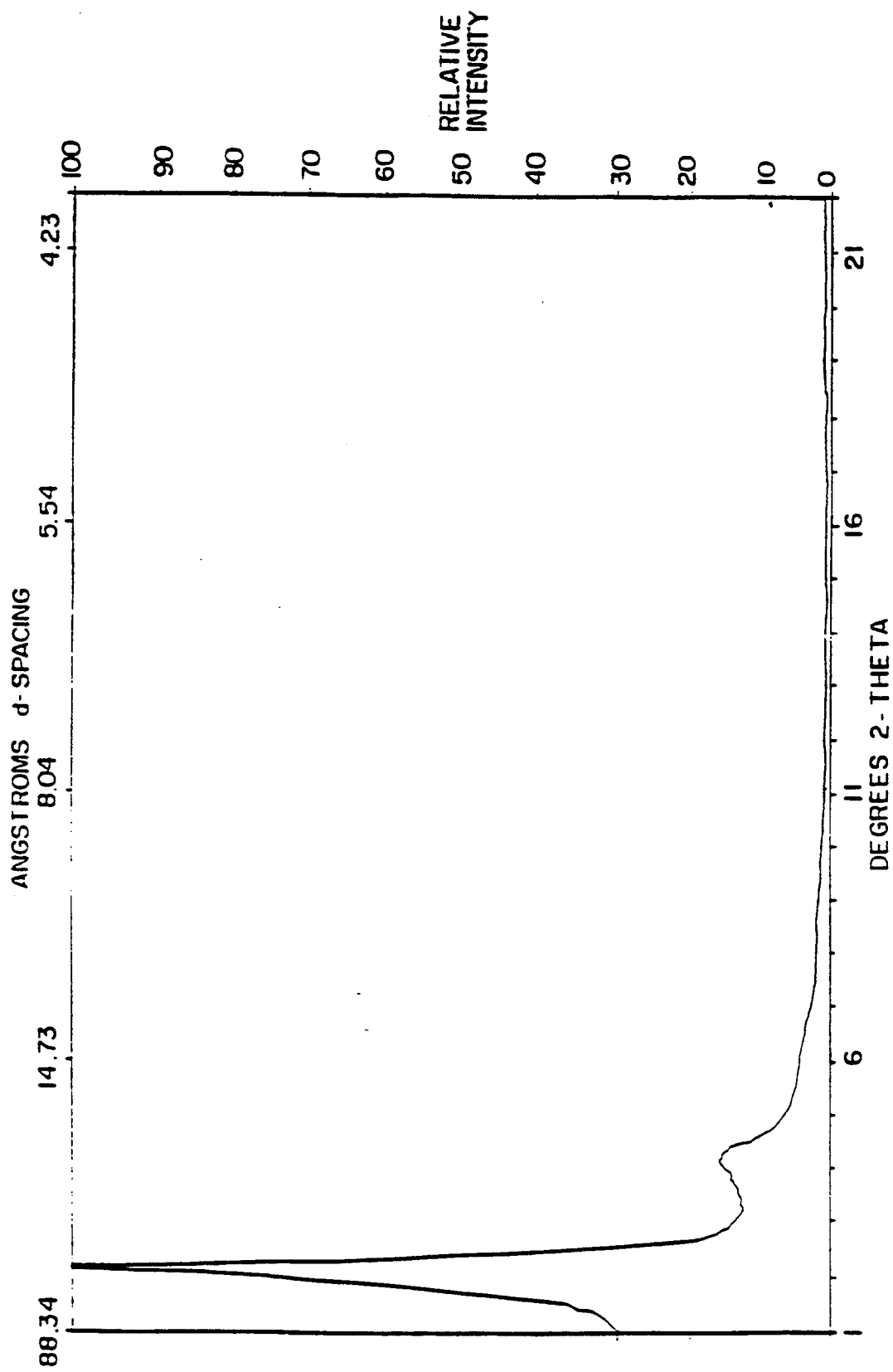

The X-ray diffraction pattern of the calcined product of this example is shown in FIG. 7. It may be characterized as including a very strong relative intensity line at 40.0±2.0 Angstroms d-spacing and a weak line at 21.2±1.0 Angstroms. TEM indicated that the product of this example contained at least three separate phases, one of which was the present ultra-large pore material.

EXAMPLE 8

A mixture of 150 grams of cetyltrimethylammonium (CTMA) hydroxide solution prepared as in Example 1 and 21 grams of colloidal silica (40%, Ludox HS-40) with an initial pH of 12.64 was heated in a 300 cc autoclave at 150° C. for 48 hours with stirring at 200 rpm. The mixture had a composition in terms of moles per mole $SiO_2$:

| |
|---|
| 0.5 mole $(CTMA)_2O$ |
| 46.5 moles $H_2O$ |

The resulting solid product was recovered by filtration, washed with water, then calcined at 540° C. for 6 hours in air.

The calcined product composition was measured to include 0.01 wt. % Na, 93.2 wt. % $SiO_2$ and 0.016 wt. % $Al_2O_3$, and proved to have a surface area of 992 m²/g and the following equilibrium adsorption capacities in grams/100 grams:

| | |
|---|---|
| $H_2O$ | 4.6 |
| Cyclohexane | >50 |
| n-Hexane | >50 |
| Benzene | 62.7 |

Figure 8:
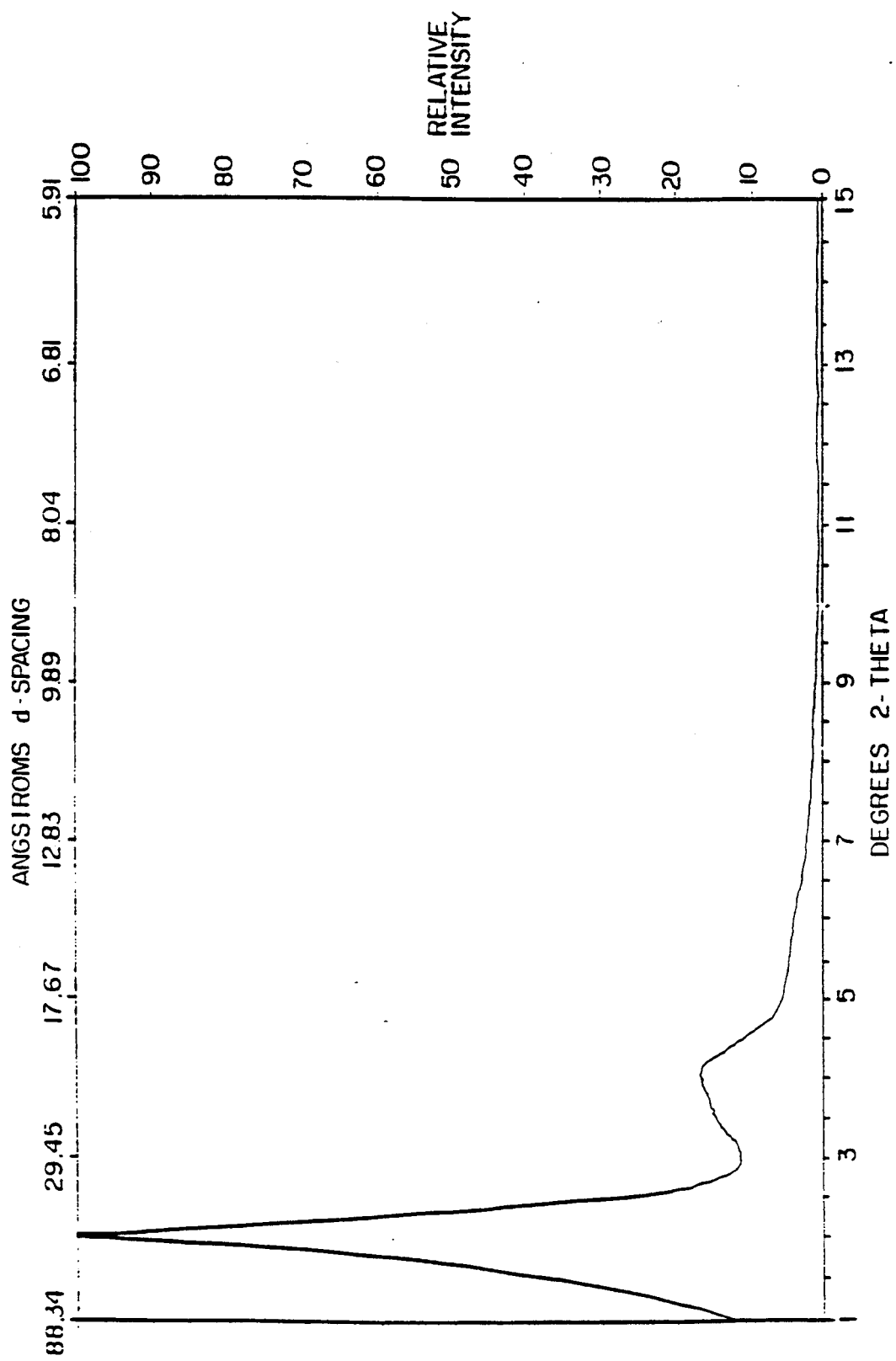

The X-ray diffraction pattern of the calcined product of this example is shown in FIG. 8. This product may be characterized as including a very strong relative intensity line at 43.6±2.0 Angstroms d-spacing and weak lines at 25.1±1.5 and 21.7±1.0 Angstroms. TEM indicated that the product contained the present ultra-large pore material.

EXAMPLE 9

Sodium aluminate (4.15 g) was added slowly into a solution containing 16 g of myristyltrimethylammonium bromide ($C_{14}$TMABr) in 100 g of water. Tetramethylammonium silicate (100 g-10% $SiO_2$), HiSil (25 g) and tetramethylammonium hydroxide (14.2 g-25% solution) were then added to the mixture. The mixture was crystallized in an autoclave at 120° C. with stirring for 24 hours.

Figure 9:
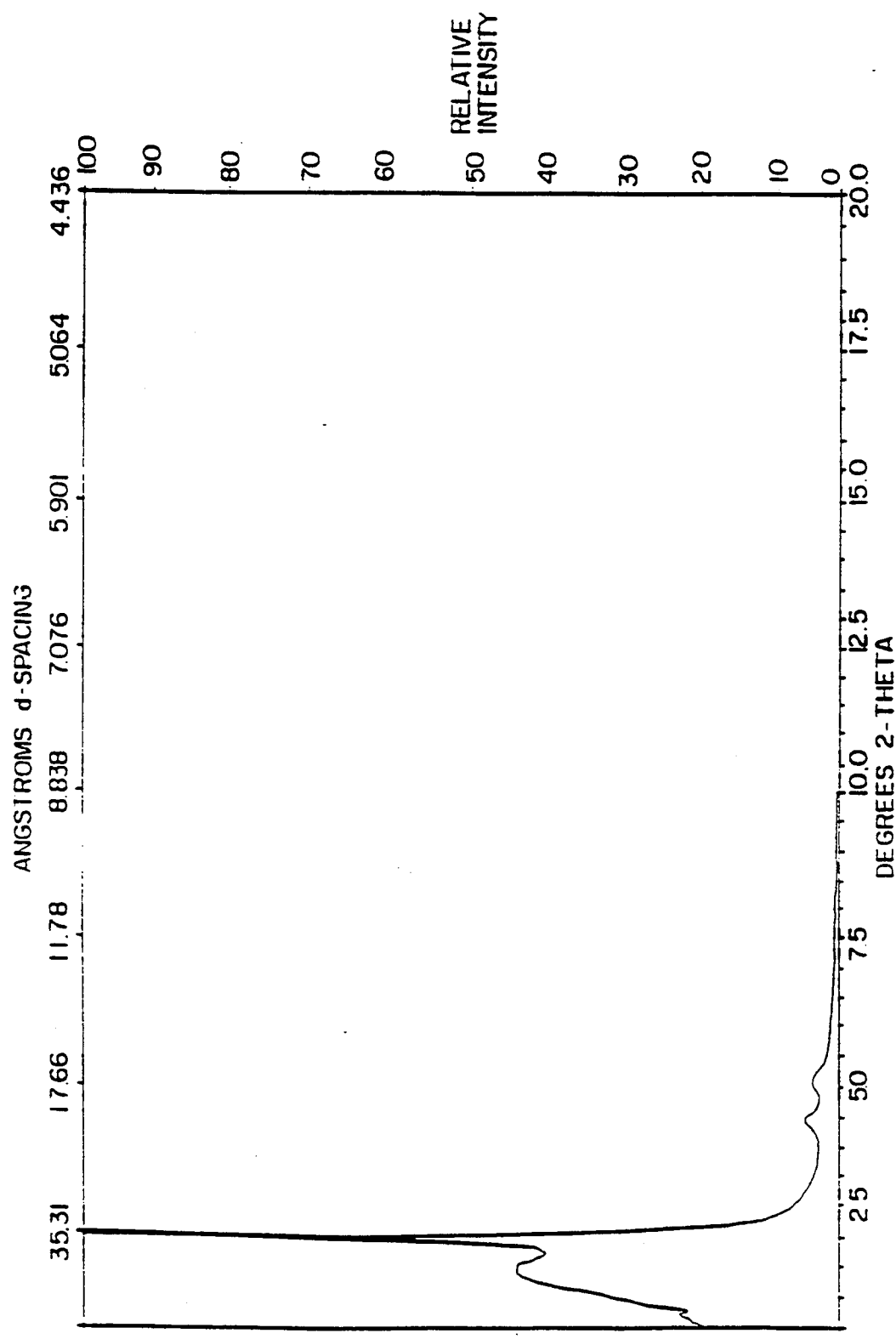

The product was filtered, washed and air dried. Elemental analysis showed the product contained 53.3 wt % $SiO_2$, 3.2 wt % $Al_2O_3$, 15.0 wt % C, 1.88 wt % N, 0.11 wt % Na and 53.5 wt % ash at 1000° C. FIG. 9 shows the X-ray diffraction pattern of the material having been calcined at 540° C. for 1 hour in $N_2$ and 6 hours in air. The X-ray diffraction pattern includes a very strong relative intensity line at 35.3±2.0 Angstroms d-spacing and weak lines at 20.4±1.0 and 17.7±1.0 Angstroms d-spacing. TEM indicated that the product contained the present ultra-large pore material.

The washed product, having been exchanged with 1N ammonium nitrate solution at room temperature, then calcined, proved to have a surface area of 827 $m^2/g$ and the following equilibrium adsorption capacities in g/100 g anhydrous sorbent:

| | |
|---|---|
| $H_2O$ | 30.8 |
| Cyclohexane | 33.0 |
| n-Hexane | 27.9 |
| Benzene | 40.7 |

EXAMPLE 10

Sodium aluminate (8.3 g) was added slowly into a solution containing 184 g of dodecyltrimethylammonium hydroxide ($C_{12}$TMAOH, 50%) solution diluted with 480 g of water. UltraSil (50 g) and an aqueous solution of tetramethylammonium silicate (200 g-10% $SiO_2$) and tetramethylammonium hydroxide (26.38 g-25% solution) were then added to the mixture. The mixture was crystallized in an autoclave at 100° C. with stirring for 24 hours.

Figure 10:
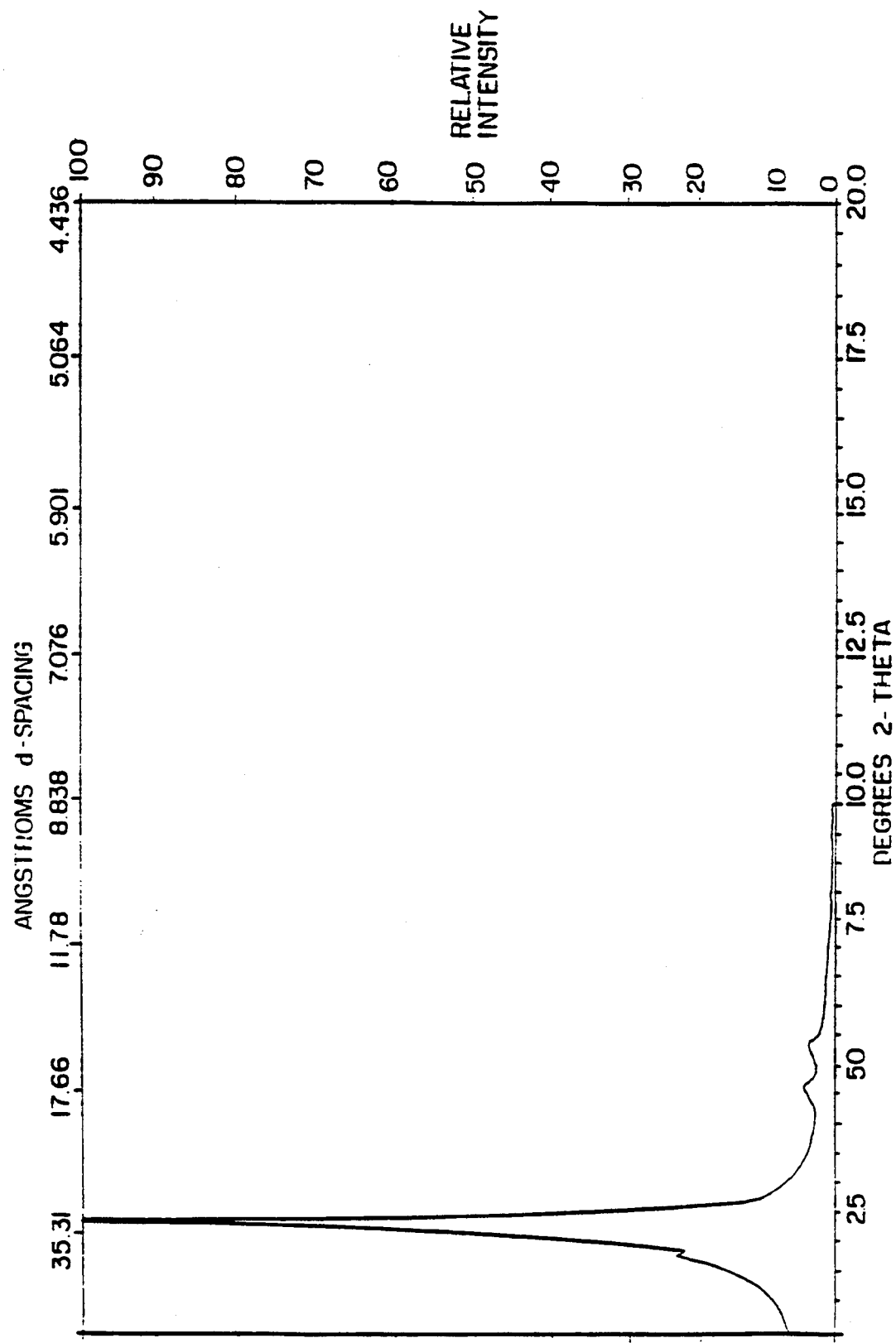

The product was filtered, washed and air dried. FIG. 10 shows the X-ray diffraction pattern of the material having been calcined at 540° C. for 1 hour in $N_2$ and 6 hours in air. The X-ray diffraction pattern includes a very strong relative intensity line at 30.4±1.5 Angstroms d-spacing and weak lines at 17.7±1.0 and 15.3±1.0 Angstroms d-spacing. TEM indicated that the product contained the present ultra-large pore material.

The washed product, having been exchanged with 1N ammonium nitrate solution at room temperature, then calcined, proved to have a surface area of 1078 $m^2/g$ and the following equilibrium adsorption capacities in g/100 g anhydrous sorbent:

| | |
|---|---|
| $H_2O$ | 32.6 |
| Cyclohexane | 38.1 |
| n-Hexane | 33.3 |
| Benzene | 42.9 |

EXAMPLE 11

A solution of 4.9 grams of $NaAlO_2$ (43.5 % $Al_2O_3$, 30% $NaO_2$) in 37.5 grams of water was mixed with 46.3 cc of 40% aqueous tetraethylammonium hydroxide solution and 96 grams of colloidal silica (40%, Ludox HS-40). The gel was stirred vigorously for 0.5 hour, mixed with an equal volume (150 ml) of cetyltrimethylammonium hydroxide solution prepared as in Example 1 and reacted at 100° C. for 168 hours. The mixture had the following composition in terms of moles per mole $Al_2O_3$:

| |
|---|
| 1.1 moles $Na_2O$ |
| 30.6 moles $SiO_2$ |
| 3.0 moles $(TEA)_2O$ |
| 3.25 moles $(CTMA)_2O$ |
| 609 moles $H_2O$ |

The resulting solid product was recovered by filtration, washed with water then calcined at 540° C. for 16 hours in air.

The calcined product proved to have a surface area of 1352 $m^2/g$ and the following equilibrium adsorption capacities in grams/100 grams:

| | |
|---|---|
| $H_2O$ | 23.6 |
| Cyclohexane | >50 |
| n-Hexane | 49 |
| Benzene | 67.5 |

Figure 11:
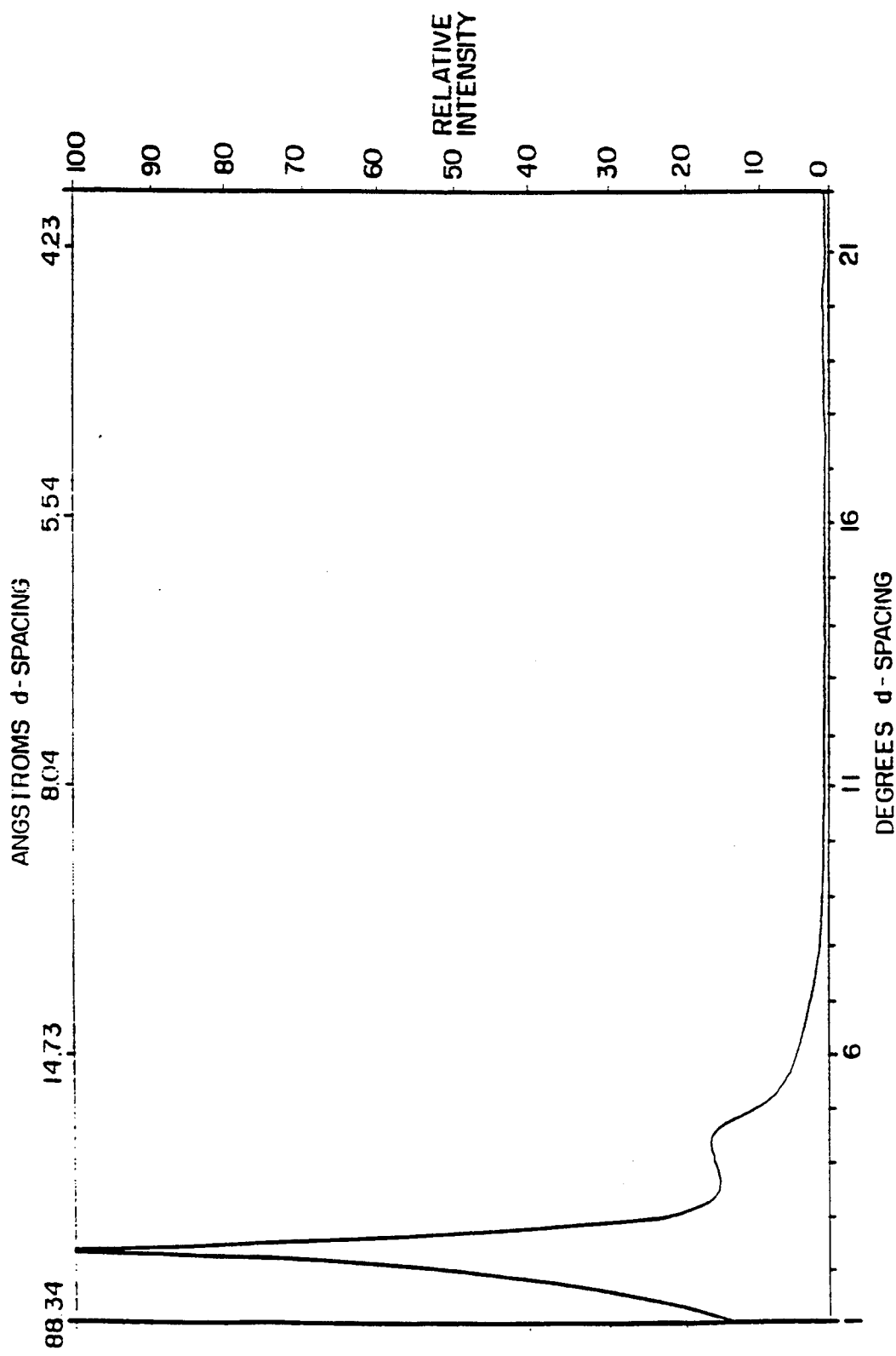

The X-ray diffraction pattern of the calcined product of this example is shown in FIG. 11. The product of this example may be characterized as including a very strong relative intensity line at 38.5±2.0 Angstroms d-spacing and a weak line at 20.3±1.0 Angstroms. TEM indicated that the product contained the present ultra-large pore material.

EXAMPLE 12

TWO hundred grams of cetyltrimethylammonium (CTMA) hydroxide solution prepared as in Example 1 was combined with 4.15 grams of sodium aluminate and 100 grams of aqueous tetramethylammonium (TMA) silicate solution (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. for 24 hours. The mixture had a composition in terms of moles per mole $Al_2O_3$:

| |
|---|
| 1.25 moles $Na_2O$ |
| 27.8 moles $SiO_2$ |
| 5.1 moles $(CTMA)_2O$ |
| 4.40 moles $(TMA)_2O$ |
| 650 moles $H_2O$ |

Figure 12:
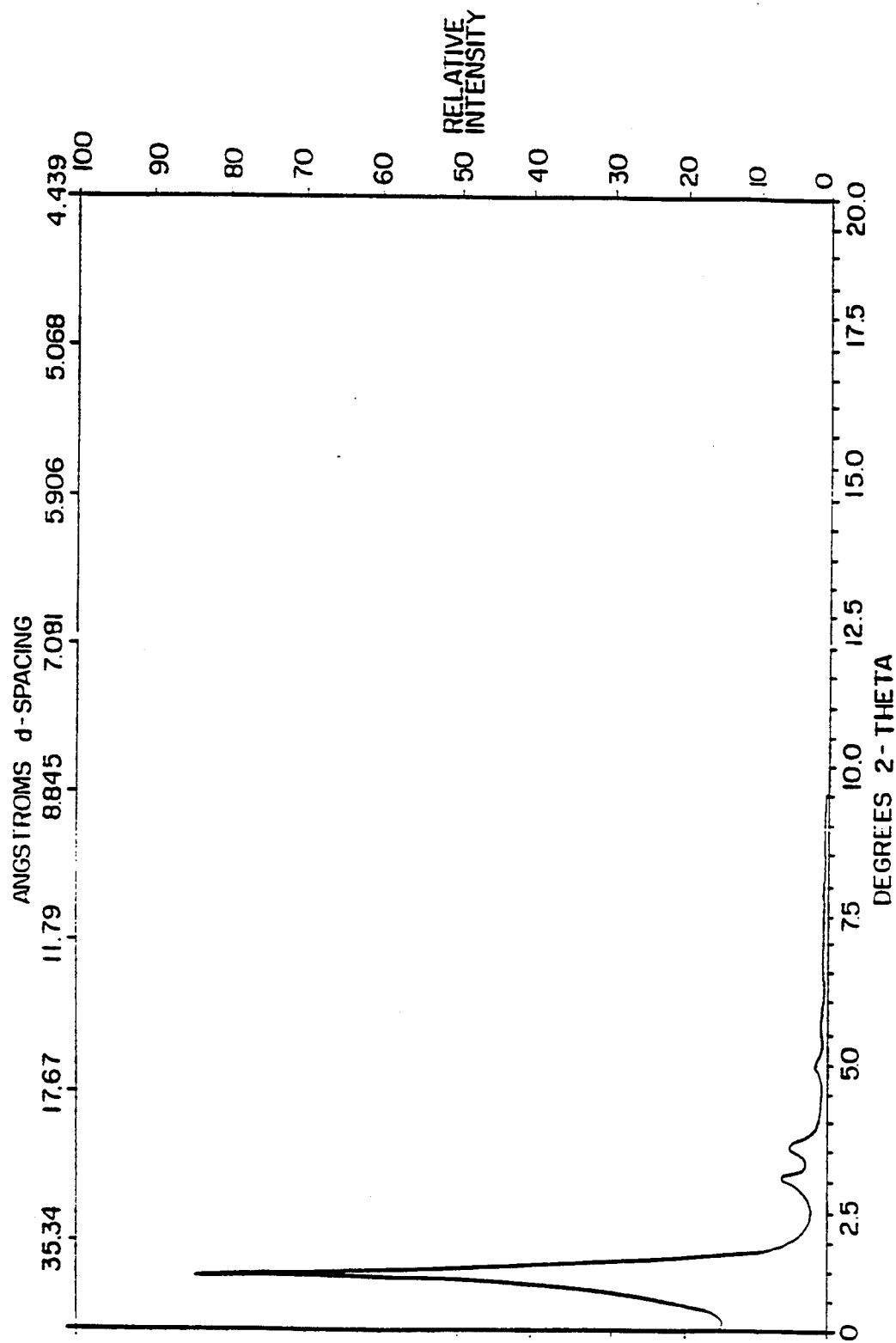

The resulting solid product was recovered by filtration and dried in air at ambient temperature. The product was then calcined at 540° C. for 1 hour in nitrogen, followed by 6 hours in air. TEM indicated that this product contained the present ultra-large pore material. The X-ray diffraction pattern of the calcined product of this example is shown in FIG. 12. This pattern can be characterized as including a very strong relative intensity line at 44.2±2.0 Angstroms d-spacing and weak lines at 25.2±1.5 and 22.0±1.0 Angstroms.

The calcined product proved to have a surface area of 932 $m^2/g$ and the following equilibrium adsorption capacities in grams/100 grams:

| | |
|---|---|
| H₂O | 39.3 |
| Cyclohexane | 46.6 |
| n-Hexane | 37.5 |
| Benzene | 50 |

The product of this example was then ammonium exchanged with 1 N NH$_4$NO$_3$ solution, followed by calcination at 540° C. for hours in air.

EXAMPLE 13

Two hundred grams of cetyltrimethylammonium (CTMA) hydroxide solution prepared as in Example 1 was combined with 4.15 grams of sodium aluminate and 100 grams of aqueous tetramethylammonium (TMA) silicate solution (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a steam box at 100° C. for 48 hours. The mixture had a composition in terms of moles per mole Al$_2$O$_3$:

| |
|---|
| 1.25 moles Na$_2$O |
| 27.8 moles SiO$_2$ |
| 5.1 moles (CTMA)$_2$O |
| 4.4 moles (TMA)$_2$O |
| 650 moles H$_2$O |

The resulting solid product was recovered by filtration and dried in air at ambient temperature. The product was then calcined at 540° C. for 1 hour in nitrogen, followed by 6 hours in air.

The calcined product proved to have the following equilibrium adsorption capacities in grams/100 grams:

| | |
|---|---|
| H$_2$O | 35.2 |
| Cyclohexane | >50 |
| n-Hexane | 40.8 |
| Benzene | 53.5 |

Figure 13:
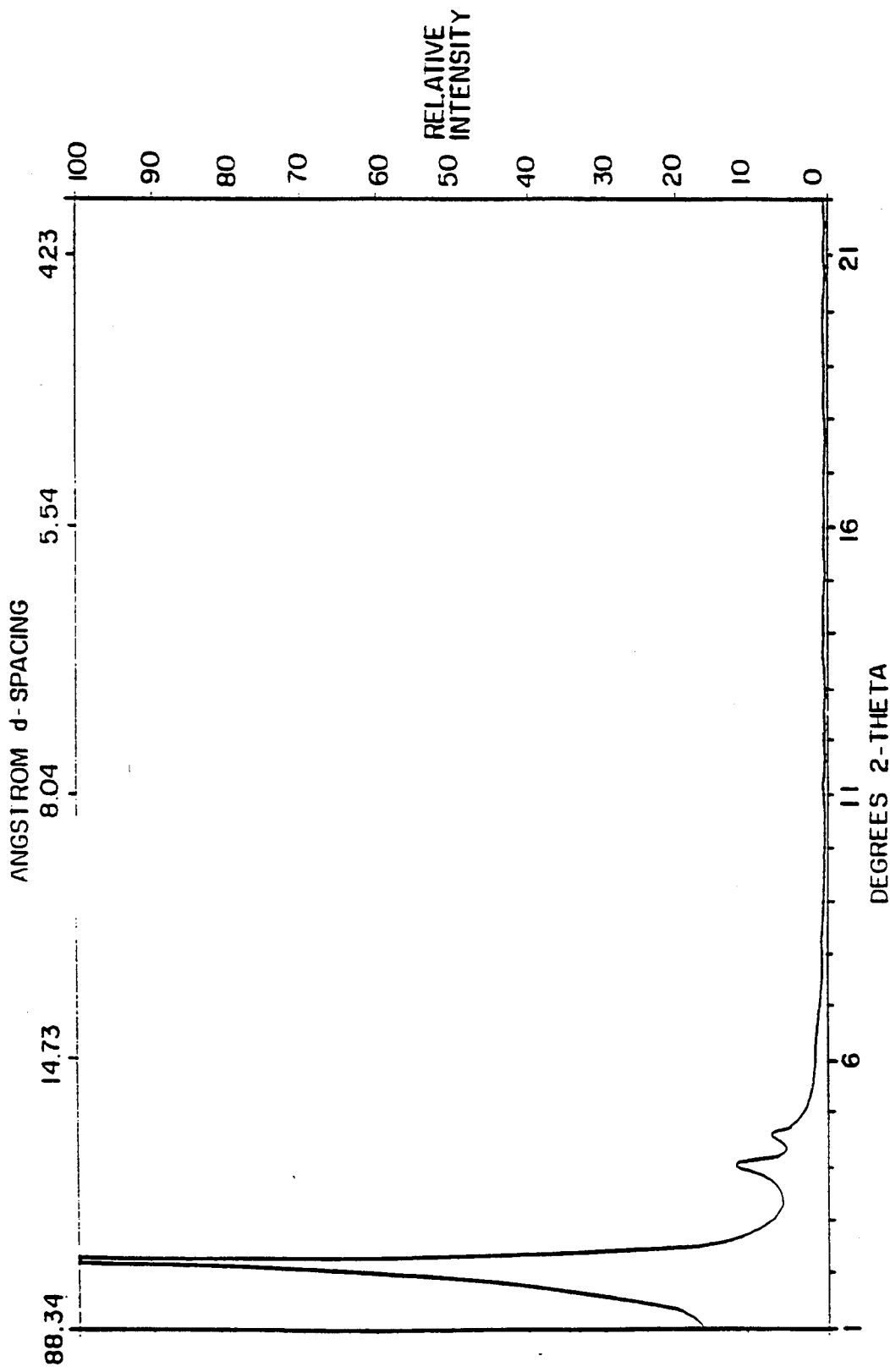

The X-ray diffraction pattern of the calcined product of this example is shown in FIG. 13. This product may be characterized as including a very strong relative intensity line at 39.1±2.0 Angstroms d-spacing and weak lines at 22.4±1.0 and 19.4±1.0 Angstroms. TEM indicated that this product contained the present ultra-large pore material.

The product of this example was then ammonium exchanged with 1 N NH$_4$NO$_3$ solution, followed by calcination at 540° C. for 10 hours in air.

EXAMPLE 14

A mixture of 125 grams of 29% CTMA chloride aqueous solution, 200 grams of water, 3 grams of sodium aluminate (in grams H$_2$O), 65 grams of Ultrasil, amorphous precipitated silica available from PQ Corporation, and 21 grams NaOH (in 50 grams H$_2$O) was stirred thoroughly and crystallized at 150° C. for 168 hours. The reaction mixture had the following relative molar composition in terms of moles per mole silica:

| |
|---|
| 0.10 moles (CTMA)$_2$O |
| 21.89 moles H$_2$O |
| 0.036 moles NaAlO$_2$ |
| 0.53 moles NaOH |

The solid product was isolated by filtration, washed with water, dried for 16 hours at room temperature and calcined at 540° C. for 10 hours in air.

The calcined product proved to have a surface area of 840 m$^2$/g, and the following equilibrium adsorption capacities in grams/100 grams:

| | |
|---|---|
| H$_2$O | 15.2 |
| Cyclohexane | 42.0 |
| n-Hexane | 26.5 |
| Benzene | 62 |

Figure 14:
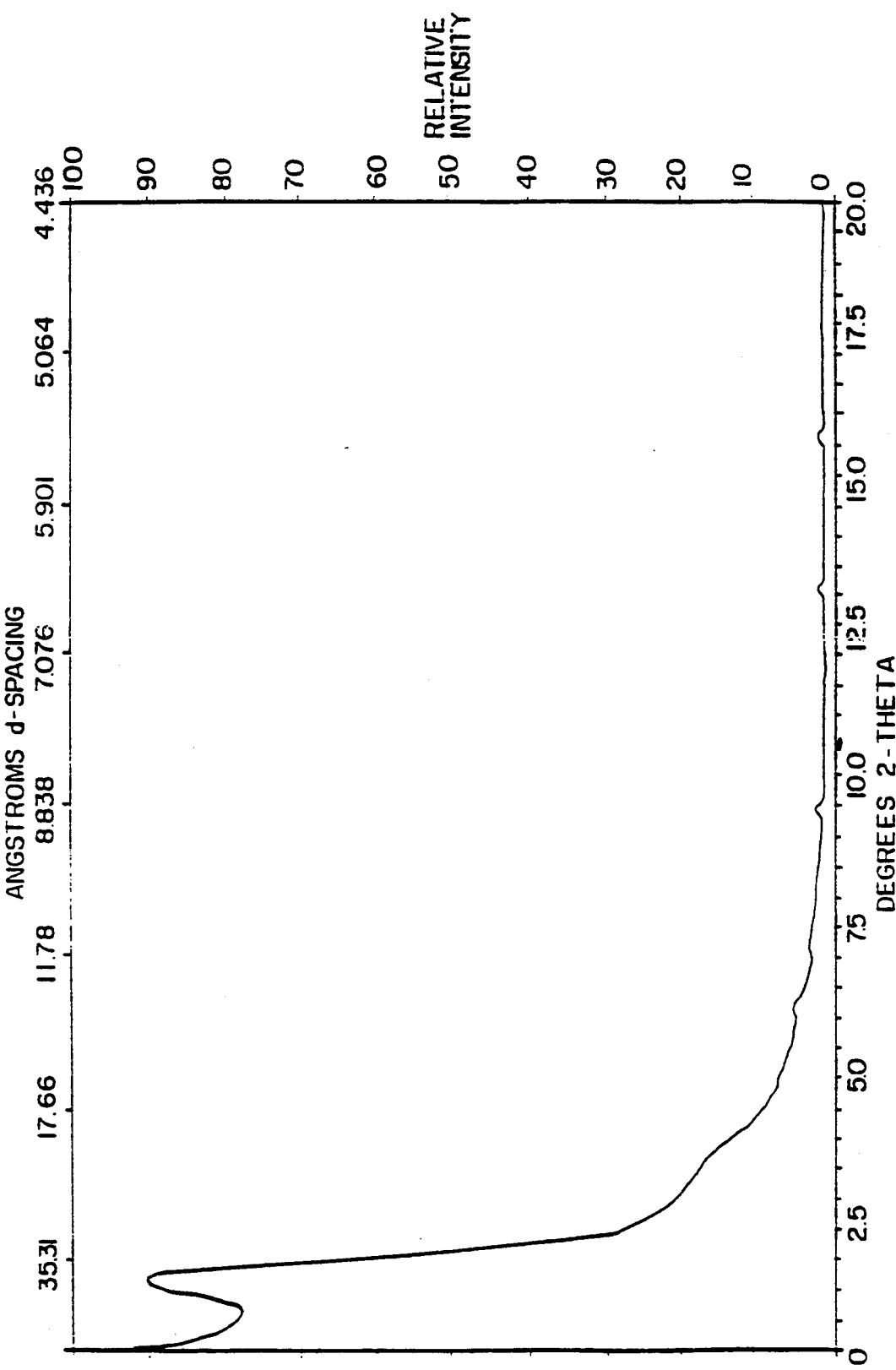

The X-ray diffraction pattern of the calcined product of this Example, shown in FIG. 14, may be characterized as including a very strong relative intensity line at 40.5±2.0 Angstroms d-spacing. TEM indicated that the product contained the present ultra-large pore material.

EXAMPLE 15

For comparison purposes, a commercially prepared ultra-stable zeolite Y was obtained. It had a benzene equilibrium adsorption capacity of 20.7 grams/100 grams. Its X-ray diffraction pattern had all the lines of zeolite Y with its highest value peak at about 14.0 Angstroms d-spacing.

EXAMPLE 16

To make the primary template mixture for this example, 240 grams of water was added to a 92 gram solution of 50% dodecyltrimethylammonium hydroxide, 36% isopropyl alcohol and 14% water such that the mole ratio of Solvent/R$_{2/f}$O was 155. The mole ratio of H$_2$O/R$_{2/f}$O in this mixture was 149 and the IPA/R$_{2/f}$O mole ratio was 6. To the primary template mixture was added 4.15 grams of sodium aluminate, 25 grams of HiSil, 100 grams of aqueous tetramethylammonium silicate solution (10% SiO$_2$) and 13.2 grams of 25% aqueous tetramethylammonium hydroxide solution. The mole ratio of R$_{2/f}$O/(SiO$_2$+Al$_2$O$_3$) was 0.28 for the mixture.

This mixture was stirred at 25° C. for 1 hour. The resulting mixture was then placed in an autoclave at 100° C. and stirred at 100 rpm for 24 hours. The mixture in the autoclave had the following relative molar composition in terms of moles per mole SiO$_2$:

| |
|---|
| 0.05 mole Na$_2$O |
| 0.036 mole Al$_2$O$_3$ |
| 0.18 mole (C$_{12}$TMA)$_2$O |
| 0.12 mole (TMA)$_2$O |
| 36.0 moles H$_2$O |
| 1.0 mole IPA |

The resulting solid product was recovered by filtration, washed with water and dried in air at ambient temperature. The product was then calcined at 540° C. for 1 hour in nitrogen, followed by 6 hours in air.

The calcined product proved to have a surface area of 1223 m$^2$/g and the following equilibrium adsorption capacities in grams/100 grams:

| | |
|---|---|
| H$_2$O | 25.5 |
| Cyclohexane | 41.1 |

| n-Hexane | 35.1 |
| Benzene | 51 |

Figure 15:
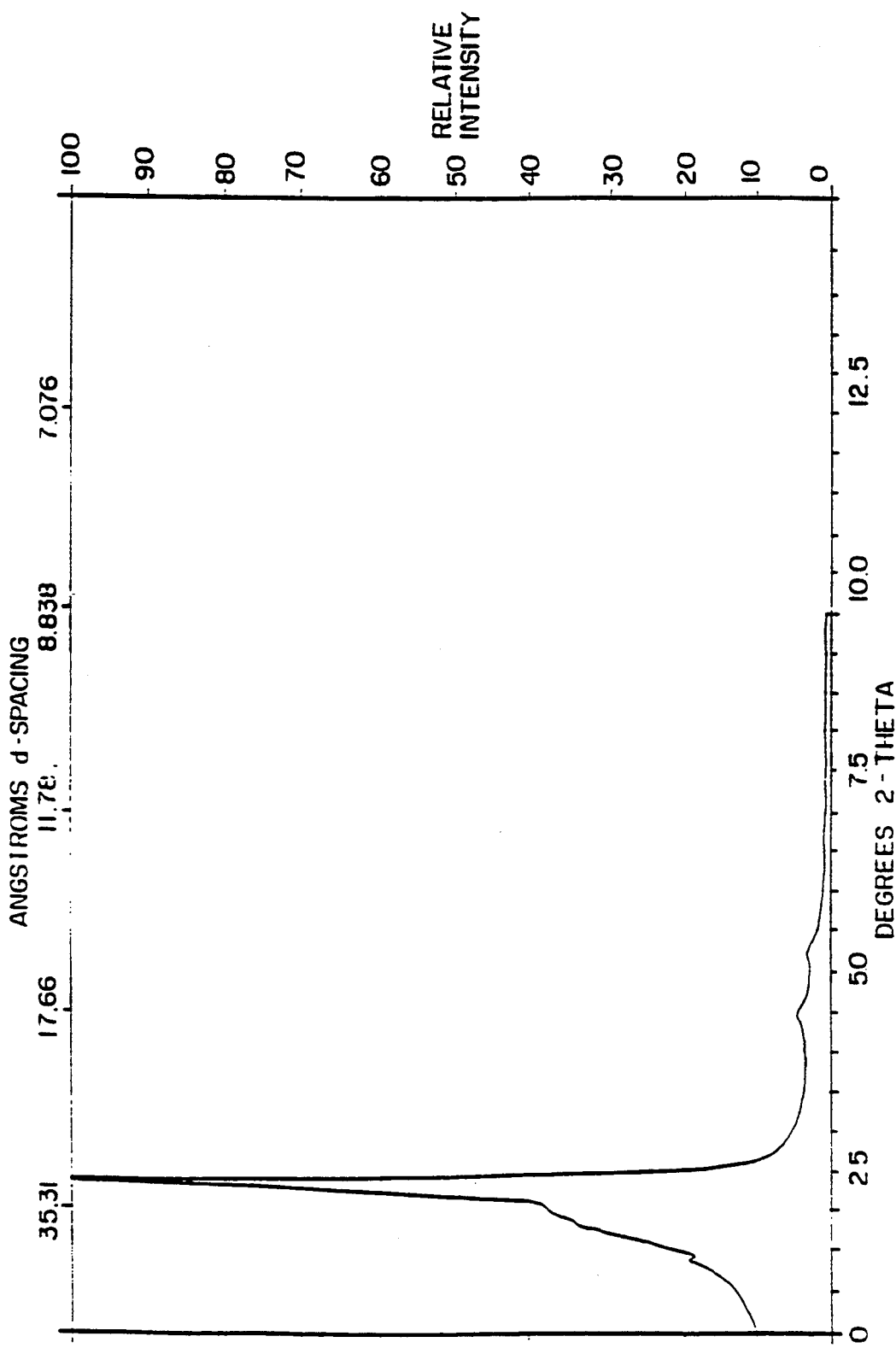

The X-ray diffraction pattern of the calcined product of this example is shown in FIG. 15. This product may be characterized as including a very strong relative intensity line at 30.8±1.5 Angstroms d-spacing and weak lines at 17.9±1.0 and 15.5±1.0 Angstroms. TEM indicated this product to contain the present ultra-large pore material.

EXAMPLE 17

A 50.75 gram quantity of decyltrimethylammonium hydroxide (prepared by contacting a ca. 29 wt. % solution of decyltrimethylammonium bromide with a hydroxide-for-halide exchange resin) was combined with 8.75 grams of tetraethylorthosilicate. The mixture was stirred for about 1 hour and then transferred to a polypropylene jar which was then placed in a steambox for about 24 hours. The mixture had a composition in terms of moles per mole $SiO_2$:

| 0.81 mole $(C_{10}TMA)_2O$ |
| 47.6 moles $H_2O$ |

The resulting solid product was filtered and washed several times with warm (60°–70° C.) distilled water and with acetone. The final product was calcined to 538° C. in $N_2$/air mixture and then held in air for about 8 hours.

The calcined product proved to have a surface area of 915 $m^2/g$ and an equilibrium benzene adsorption capacity of 35 grams/100 grams. Argon physisorption data indicated an argon uptake of 0.34 cc/gram, and a pore size of 15 Angstroms.

The X-ray diffraction pattern of the calcined product of this example may be characterized as including a very strong relative intensity line at 27.5±1.5 Angstroms d-spacing and weak lines at 15.8±1.0 and 13.7±1.0 Angstroms. TEM indicated that the product of this example contained the present ultra-large pore material.

EXAMPLE 18

To eighty grams of cetyltrimethylammonium hydroxide (CTMAOH) solution prepared as in Example 1 was added 1.65 grams of $NaAlO_2$. The mixture was stirred at room temperature until the $NaAlO_2$ was dissolved. To this solution was added 40 grams of aqueous tetramethylammonium (TMA) silicate solution (10 wt. % $SiO_2$), 10 grams of HiSil, 200 grams of water and 70 grams of 1,3,5-trimethylbenzene (mesitylene). The resulting mixture was stirred at room temperature for several minutes. The gel was then loaded into a 600 cc autoclave and heated at 105° C. for sixty-eight hours with stirring at 150 rpm. The mixture had a composition in terms of moles per mole $Al_2O_3$:

| 1.2 moles $Na_2O$ |
| 27.8 moles $SiO_2$ |
| 5.1 moles $(CTMA)_2O$ |
| 2.24 moles $(TMA)_2O$ |
| 2256 moles $H_2O$ |
| 80.53 moles 1,3,5-trimethylbenzene |

The resulting product was filtered and washed several times with warm (60°–70° C.) distilled water and with acetone. The final product was calcined to 538° C. in $N_2$/air mixture and then held in air for about 10 hours.

The calcined product proved to have an equilbrium benzene adsorption capacity of >25 grams/100 grams.

The X-ray diffraction pattern of the calcined product of this example may be characterized as including a broad, very strong relative intensity line at about 102 Angstroms d-spacing, but accurate positions of lines in the extreme low angle region of the X-ray diffraction pattern are very difficult to determine with conventional X-ray diffractometers. Furthermore, finer collimating slits were required to resolve a peak at this low 2-theta angle. The slits used in this example, starting at the X-ray tube, were 0.1, 0.3, 0.5 and 0.2 mm, respectively. TEM indicated that the product of this example contained several materials with different $d_{100}$ values as observed in their electron diffraction patterns. These materials were found to possess $d_{100}$ values between about 85 Angstroms d-spacing and about 120 Angstroms d-spacing.

EXAMPLE 19

To eighty grams of cetyltrimethylammonium hydroxide (CTMAOH) solution prepared as in Example 1 was added 1.65 grams of $NaAlO_2$. The mixture was stirred at room temperature until the $NaAlO_2$ was dissolved. To this solution was added 40 grams of aqueous tetramethylammonium (TMA) silicate solution (10 wt. % $SiO_2$), 10 grams of HiSil, 200 grams of water and 120 grams of 1,3,5-trimethylbenzene (mesitylene). The resulting mixture was stirred at room temperature for several minutes. The gel was then loaded into a 600 cc autoclave and heated at 105° C. for ninety hours with stirring at 150 rpm. The mixture had a composition in terms of moles per mole $Al_2O_3$:

| 1.25 moles $Na_2O$ |
| 27.8 moles $SiO_2$ |
| 5.1 moles $(CTMA)_2O$ |
| 2.24 moles $(TMA)_2O$ |
| 2256 moles $H_2O$ |
| 132.7 moles 1,3,5-trimethylbenzene |

The resulting product was filtered and washed several times with warm (60°–70° C.) distilled water and with acetone. The final product was calcined to 538° C. in $N_2$/air mixture and then held in air for about 10 hours.

The calcined product proved to have a surface area of 915 $m^2/g$ and an equilbrium benzene adsorption capacity of >25 grams/100 grams. Argon physisorption data indicated an argon uptake of 0.95 cc/gram, and a pore size centered on 78 Angstroms (Dollimore-Heal Method, see Example 22(b)), but running from 70 to greater than 105 Angstoms.

The X-ray diffraction pattern of the calcined product of this example may be characterized as having only enhanced scattered intensity in the very low angle region of the X-ray diffraction, where intensity from the transmitted incident X-ray beam is usually observed. However, TEM indicated that the product of this example contained several materials with different $d_{100}$ values as observed in their electron diffraction patterns. These materials were found to possess $d_{100}$ values between about 85 Angstroms d-spacing and about 110 Angstroms d-spacing.

EXAMPLE 20

To eighty grams of cetyltrimethylammonium hydroxide (CTMAOH) solution prepared as in Example 1 was added 1.65 grams of NaAlO$_2$. The mixture was stirred at room temperature until the NaAlO$_2$ was dissolved. To this solution was added 40 grams of aqueous tetramethylammonium (TMA) silicate solution (10 wt. % SiO$_2$), 10 grams of HiSil, and 18 grams of 1,3,5-trimethylbenzene (mesitylene). The resulting mixture was stirred at room temperature for several minutes. The gel was then loaded into a 300 cc autoclave and heated at 105° C. for four hours with stirring at 150 rpm. The mixture had a composition in terms of moles per mole Al$_2$O$_3$:

| |
|---|
| 1.25 moles Na$_2$O |
| 27.8 moles SiO$_2$ |
| 5.1 moles (CTMA)$_2$O |
| 2.24 moles (TMA)$_2$O |
| 650 moles H$_2$O |
| 19.9 moles 1,3,5-trimethylbenzene |

The resulting product was filtered and washed several times with warm (60°–70° C.) distilled water and with acetone. The final product was calcined to 538° C. in N$_2$/air mixture and then held in air for about 8 hours.

The calcined product proved to have a surface area of 975 m$^2$/g and an equilbrium benzene adsorption capacity of >40 grams/100 grams. Argon physisorption data indicated an argon uptake of 0.97 cc/gram, and a pore size of 63 Angstroms (Dollimore-Heal Method, see Example 22(b)), with the peak occurring at P/P$_o$=0.65.

The X-ray diffraction pattern of the calcined product of this example may be characterized as including a very strong relative intensity line at 63±5 Angstroms d-spacing and weak lines at 36.4±2.0, 31.3±1.5 Angstroms and 23.8±1.0 Angstroms d-spacing. TEM indicated that the product of this example contained the present ultra-large pore material.

EXAMPLE 21

For catalytic evaluation of the present invention, final products from Examples 1 through 15 were evaluated for dealkylation of tri-tert-butylbenzene (TBB) to di-tert butylbenzene. The present evaluation was conducted under one or both of two sets of conditions: (i) at a temperature of 225° C., weight hourly space velocity of 100 hr$^{-1}$ or (ii) at a temperature of 200° C., weight hourly space velocity of 200 hr$^{-1}$. Pressure was atmospheric. The feed was composed of 6.3/93.7 TTBB/toluene. Conversion was measured at 30 minutes on stream.

The results were as follows:

| Catalyst of | Conversion, wt. % | |
|---|---|---|
| Example | 225° C./100 hr$^{-1}$ | 200° C./200 hr$^{-1}$ |
| 1 | 0 | — |
| 2 | 6.2 | — |
| 3 | 53.9 | — |
| 4 | 10.4 | — |
| 5 | 68.9 | — |
| 6 | 100.0 | — |
| 7 | 93.4 | 66.0 |
| 8 | 5.3 | — |
| 9 | — | 61.2 |
| 10 | — | 58.9 |
| 11 | 86.3 | — |
| 12 | 96.7 | — |

-continued

| Catalyst of | Conversion, wt. % | |
|---|---|---|
| Example | 225° C./100 hr$^{-1}$ | 200° C./200 hr$^{-1}$ |
| 13 | 92.8 | — |
| 14 | — | 37.7 |
| 15 | 12.0 | 0 |

EXAMPLE 22(a)

Argon Physisorption For Pore Systems Up to About 60 Angstroms Diameter

To determine the pore diameters of the products of this invention with pores up to about 60 Angstroms in diameter, 0.2 gram samples of the products of Examples 1 through 17 were placed in glass sample tubes and attached to a physisorption apparatus as described in U.S. Pat. No. 4,762,010, which is incorporated herein by reference.

Figure 16:
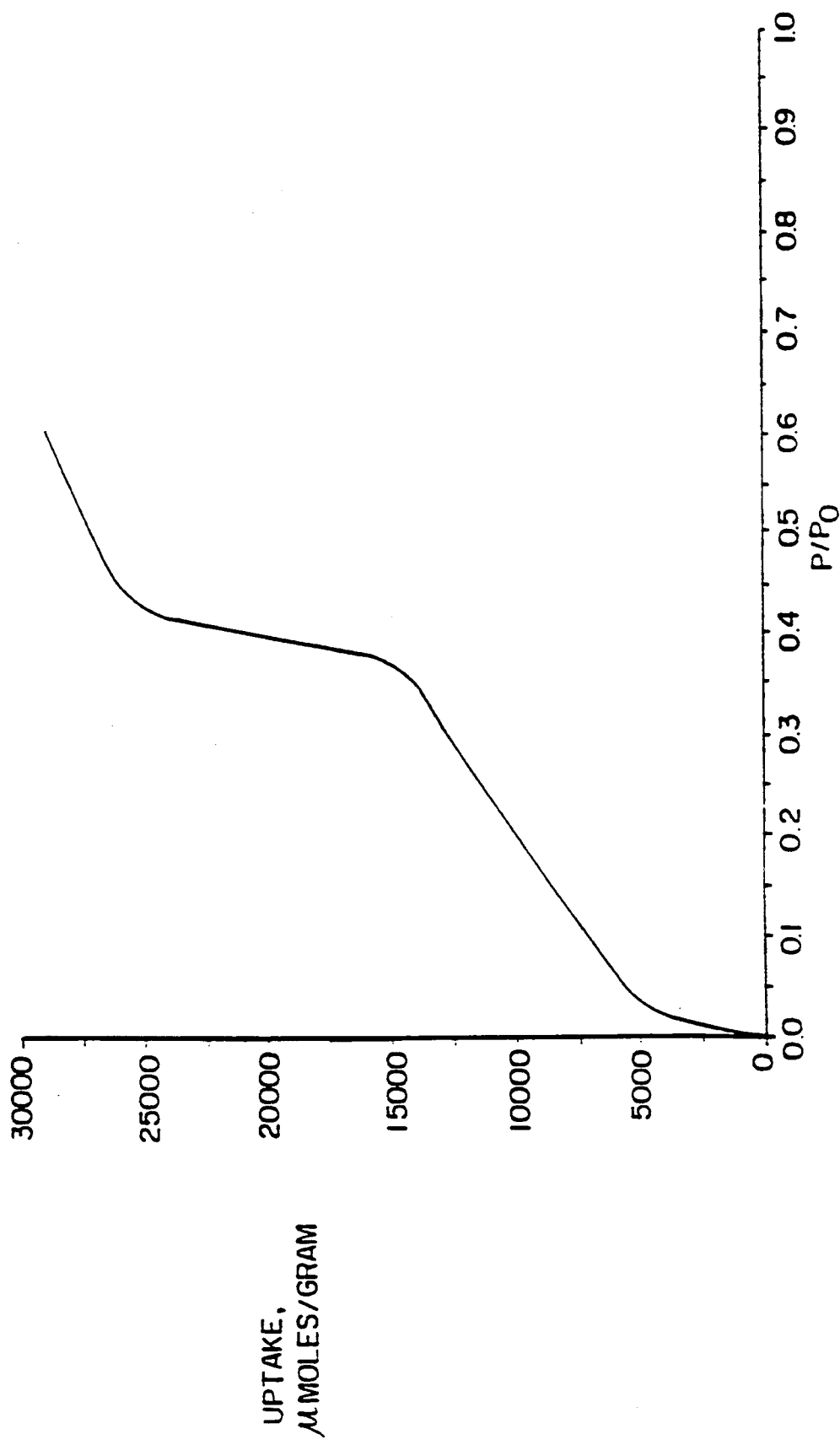
FIG. 16 is an isotherm plot of physisorption measurements from Example 22.

The samples were heated to 300° C. for 3 hours in vacuo to remove adsorbed water. Thereafter, the samples were cooled to 87° K. by immersion of the sample tubes in liquid argon. Metered amounts of gaseous argon were then admitted to the samples in stepwise manner as described in U.S. Pat. No. 4,762,010, column 20. From the amount of argon admitted to the samples and the amount of argon left in the gas space above the samples, the amount of argon adsorbed can be calculated. For this calculation, the ideal gas law and the calibrated sample volumes were used. (See also S. J. Gregg et al., Adsorption, Surface Area and Porosity, 2nd ed., Academic Press, 1982). In each instance, a graph of the amount adsorbed versus the relative pressure above the sample, at equilibrium, constitutes the adsorption isotherm as shown in FIG. 16 for the Example 4 product sample. It is common to use relative pressures which are obtained by forming the ratio of the equilibrium pressure and the vapor pressure P$_o$ of the adsorbate at the temperature where the isotherm is measured. Sufficiently small amounts of argon were admitted in each step to generate 168 data points in the relative pressure range from 0 to 0.6. At least about 100 points are required to define the isotherm with sufficient detail.

Figure 17:
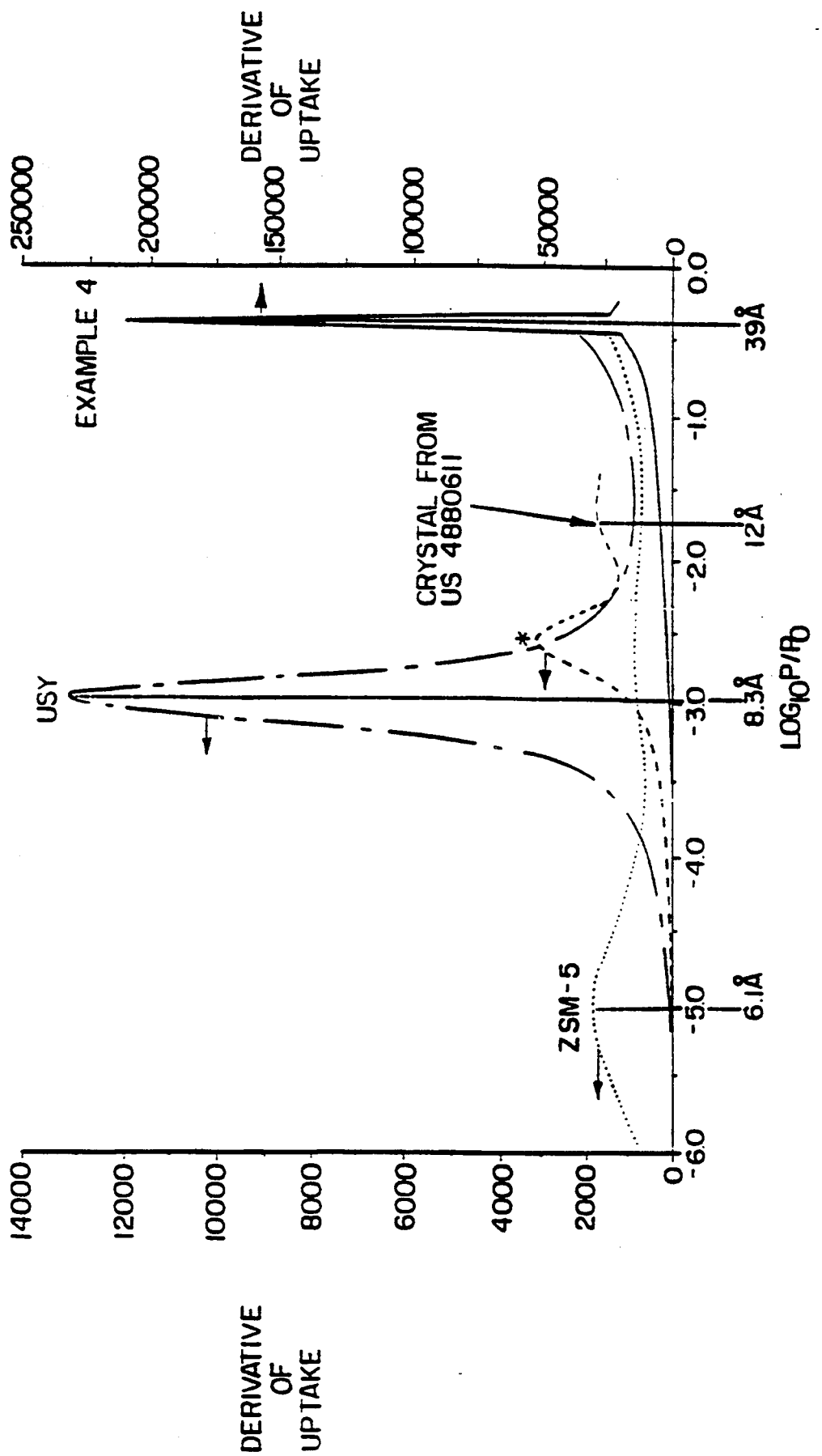
FIG. 17 is a plot of physisorption measurements from Example 22 showing pore sizes of various crystalline materials.

The step (inflection) in the isotherm, in this case (Example 4 product) at about P/P$_o$=0.4, indicates filling of a pore system. The size of the step indicates the amount adsorbed, whereas the position of the step in terms of P/P$_o$ reflects the size of the pores in which the adsorption takes place. Larger pores are filled at higher P/P$_o$. In order to better locate the position of the step in the isotherm, the derivative with respect to log (P/P$_o$) is formed. This is shown in FIG. 17. Also shown in FIG. 17 are data obtained in an identical fashion for a crystalline material from U.S. Pat. No. 4,880,611 and several other crystal materials. There is further provided a physical scale on the axis which converts the position of an adsorption peak in terms of log (P/P$_o$) to the physical pore diameter in Angstroms. This conversion was obtained by using the following formula:

$$\log(P/P_o) = \frac{K}{d - 0.38}\left(\frac{S^4}{3(L - D/2)^3} - \frac{S^{10}}{9(L - D/2)^9} - \right.$$

-continued $$\left. \frac{S^4}{3\,(D/2)^3} + \frac{S^{10}}{9\,(D/2)^9} \right)$$

wherein d=pore diameter in nanometers, K=32.17, S=0.2446, L=d+0.19, and D=0.57.

This formula is derived from the method of Horvath and Kawazoe (G. Horvath et al., *J. Chem. Eng. Japan*, 16 (6) 470(1983)). The constants required for the implementation of this formula were determined from a measured isotherm of ALPO-5 and its known pore size. This method is particularly useful for microporous materials having pores of up to about 60 Angstroms in diameter.

As is indicated in FIG. 17, the pore size of the material of Example 4 is 39.6 Angstroms with the peak occurring at log $(P/P_o) = -0.4$ or $P/P_o = 0.4$, while the pore size of the material from U.S. Pat. 4,880,611 is 12 Angstroms or $P/P_o = 0.02$. In the other materials, a peak is observed at $P/P_o = 0.015$ which is denoted by an asterisk in FIG. 17. This peak reflects adsorption on the walls of the pores and is not otherwise indicative of the size of the pores of a given material. A value of $P/P_o$ of 0.03 corresponds to 13 Angstroms pore size.

The results of this procedure for the samples from Examples 1 through 17 are tabulated below. The samples from Examples 10, 13 and 16 gave two separate peaks, believed to be the result of two separate ultra-large pore phases in the products.

| Examples | Pore Diameter, Angstroms |
|---|---|
| 1 | 32.2 |
| 2 | 35.4 |
| 3 | 42.5 |
| 4 | 39.6. |
| 5 | 16.9 |
| 6 | 27.3 |
| 7 | 36.6 |
| 8 | 42.6 |
| 9 | 28.3 |
| 10 | 22.8, 30.8 |
| 11 | 36.8 |
| 12 | 36.1 |
| 13 | 35.0, 42.1 |
| 14 | 40.0 |
| 15 | 8.3 |
| 16 | 22.4, 30.4 |
| 17 | 15.0 |

EXAMPLE 22(b)

Argon Physisorption For Pore Systems Over About 60 Angstroms Diameter

The above method of Horvath and Kawazoe for determining pore size from physisorption isotherms was intended to be applied to pore systems of up to 20 Angstroms diameter; but with some care as above detailed, its use can be extended to pores of up to 60 Angstroms diameter.

In the pore regime above 60 Angstroms diameter, however, the Kelvin equation can be applied. It is usually given as:

$$\ln(P/P_o) = \frac{-2\gamma v}{r_k RT} \cos \Theta$$

where:
γ = surface tension of sorbate
V = molar volume of sorbate
Θ = contact angle (usually taken for practical reasons to be 0)
R = gas constant
T = absolute temperature
$r_k$ = capillary condensate (pore) radius
$P/P_o$ = relative pressure (taken from the physisorption isotherm)

The Kelvin equation treats adsorption in pore systems as a capillary condensation phenomenon and relates the pressure at which adsorption takes place to the pore diameter through the surface tension and contact angle of the adsorbate (in this case, argon). The principles upon which the Kelvin equation are based are valid for pores in the size range 50 to 1000 Angstrom diameter. Below this range the equation no longer reflects physical reality, since true capillary condensation cannot occur in smaller pores; above this range the logarithmic nature of the equation precludes obtaining sufficient accuracy for pore size determination.

The particular implementation of the Kelvin equation often chosen for measurement of pore size is that reported by Dollimore and Heal (D. Dollimore and G. R. Heal, *J. Applied Chem*, 14, 108 (1964)). This method corrects for the effects of the surface layer of adsorbate on the pore wall, of which the Kelvin equation proper does not take account, and thus provides a more accurate measurement of pore diameter. While the method of Dollimore and Heal was derived for use on desorption isotherms, it can be applied equally well to adsorption isotherms by simply inverting the data set. The products of Examples 19 and 20 were subjected to the Dollimore and Heal Method for argon physisorption data, as indicated.

EXAMPLE 23

Transmission Electron Microscopy

To further illustrate the nature of the crystalline product of this invention, samples of the products from Examples 1 through 14 and 16 through 20 were studied by transmission electron microscopy (TEM) as noted above. TEM is a technique used to reveal the microscopic structure of materials, including crystalline materials.

In order to illuminate the microstructure of materials, samples must be thin enough for an electron beam to pass through them, generally about 500-1000 Angstrom units or so thick. The crystal morphology of the present materials usually required that they be prepared for study by ultramicrotomy. While time consuming, this technique of sample preparation is quite familiar to those skilled in the art of electron microscopy. The materials are embedded in a resin, in this case a commercially available low viscosity acrylic resin L. R. WHITE (hard), which is then cured at about 80° C. for about 1½ hours. Thin sections of the block are cut on an ultramicrotome using a diamond knife and sections in the thickness range 500-1000 Angstrom units are collected on fine mesh electron microscope support grids. For these materials, an LKB model microtome with a 45° C. diamond knife edge was used; the support grids were 400 mesh copper grids. After evaporation of a thin carbon coating on the sample to prevent charging in the microscope (light gray color on a white sheet of paper next to the sample in the evaporator), the samples are ready for examination in the TEM.

High resolution TEM micrographs show projections of structure along the direction that the sample is viewed. For this reason, it is necessary to have a sample in specific orientations to see certain details of the microstructure of the material. For crystalline materials, these orientations are most easily chosen by observing the electron diffraction pattern (EDP) that is produced simultaneously with the electron microscope image. Such EDP's are readily produced on modern TEM instruments using, e.g. the selected area field limiting aperture technique familiar to those skilled in the art of electron microscopy. When an EDP with the desired arrangement of diffraction spots is observed, the corresponding image of the crystal giving that EDP will reveal details of the microstructure along the direction of projection indicated by the EDP. In this way, different projections of a crystal's structure can be observed and identified using TEM.

Figure 18:
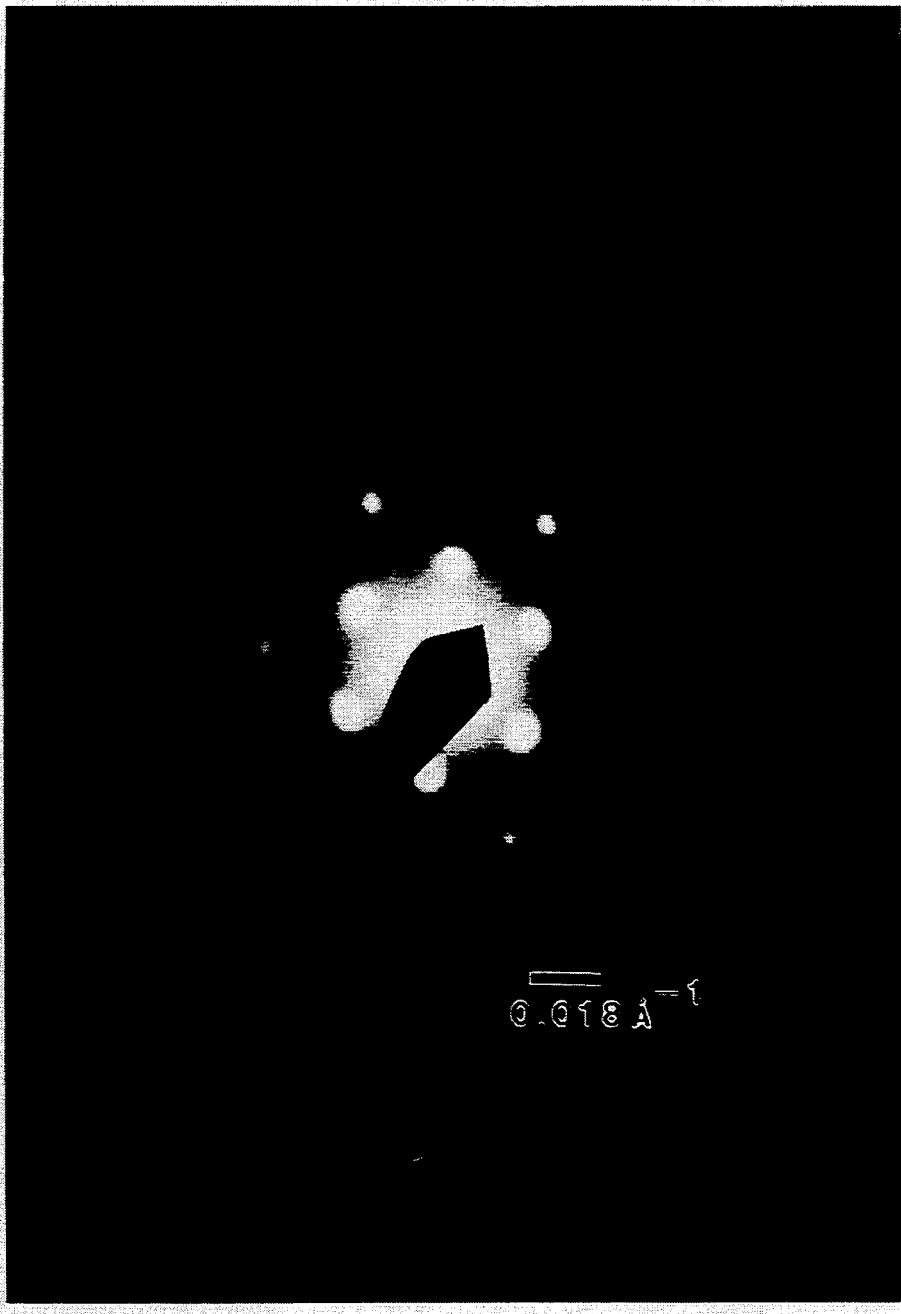
FIG. 18 is an electron diffraction pattern of the product of Example 4.

In order to observe the salient features of the crystalline product of the present invention, it is necessary to view the material in an orientation wherein the corresponding EDP gives a hexagonal arrangement of diffraction spots from a single individual crystal. If multiple crystals are present within the field limiting aperture, overlapping diffraction patterns will occur that can be quite difficult to interpret. An example of a hexagonal pattern from an individual crystal from the product in Example 4 is shown in FIG. 18. The number of diffraction spots observed depends to a degree upon the regularity of the crystalline arrangement in the material, among other things. At the very least, however, the inner ring of bright spots should be observed to obtain a good image. Individual crystals can be manipulated by specimen tilt adjustments on the TEM until this orientation is achieved. More often, it is easier to take advantage of the fact that the specimen contains many randomly oriented crystals and to simply search through the sample until a crystal giving the desired EDP (and hence orientation) is located. This latter technique was used to produce the electron micrographs discussed below.

Figure 19:
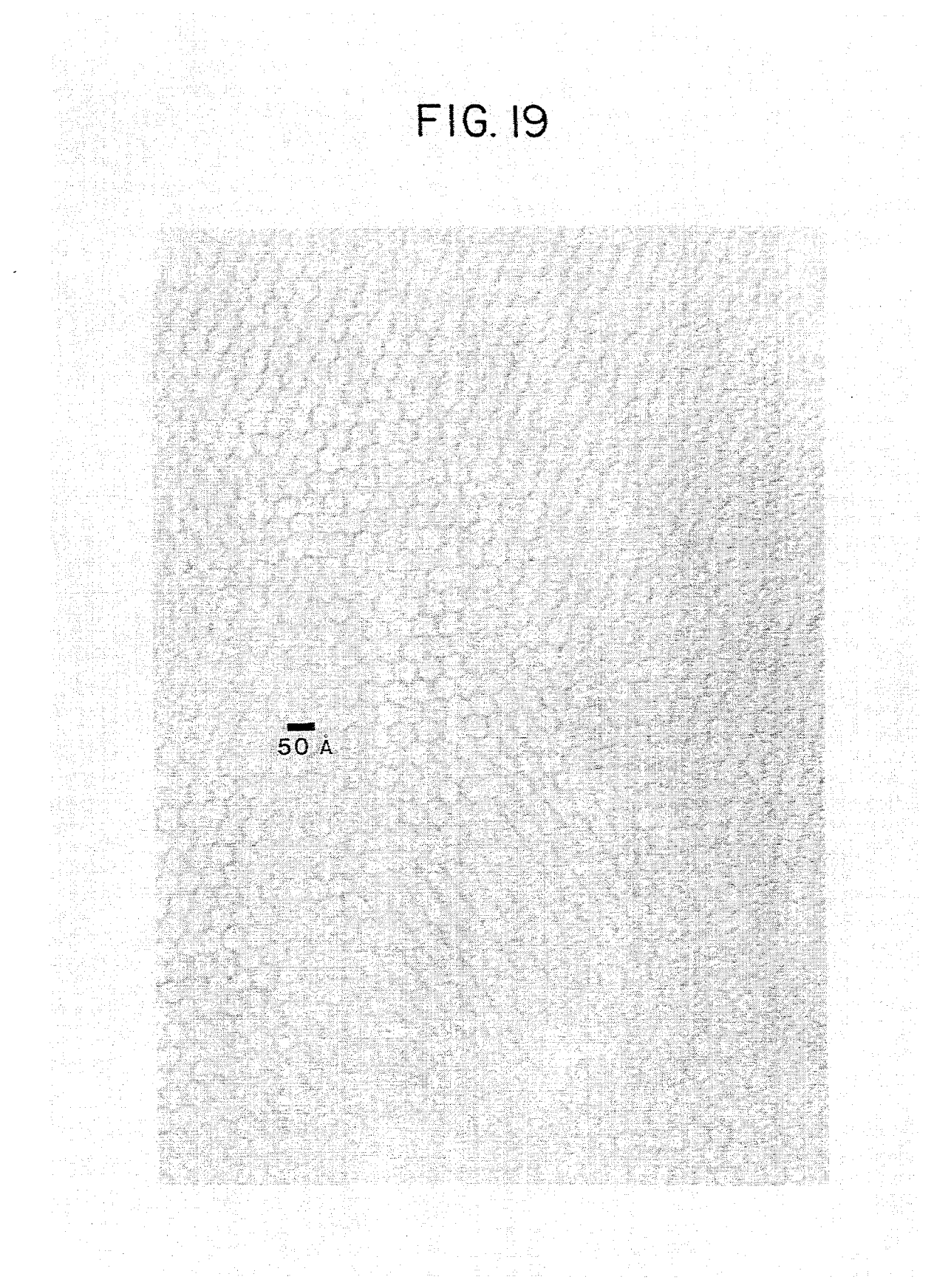

Microtomed samples of materials from the Examples were examined by the techniques described above in a JEOL 200 CX transmission electron microscope operated at 200,000 volts with an effective 2 Angstrom objective aperture in place. The instrument has a point-to-point resolution of 4.5 Angstroms. Other experimental arrangements familiar to one skilled in the art of high resolution (phase contrast) TEM could be used to produce equivalent images provided care is taken to keep the objective lens on the underfocus (weak leans) side of the minimum contrast lens current setting. FIG. 19 is an electron micrograph from a microtomed thin section of the crystalline product from Example 4. This micrograph shows a reasonably regular array of large channels in a hexagonal arrangement. The repeat distance between the channels is about 45 Angstrom units, which is consistent with the position of the first peak in the X-ray diffraction pattern (41 Angstroms/$\sqrt{3}/2$) of this material. Since the channels must have walls between them, this observation is also consistent with the estimated pore size of about 39.6 Angstrom units calculated from Argon physisorption measurements of this material in Example 17.

Figure 20:
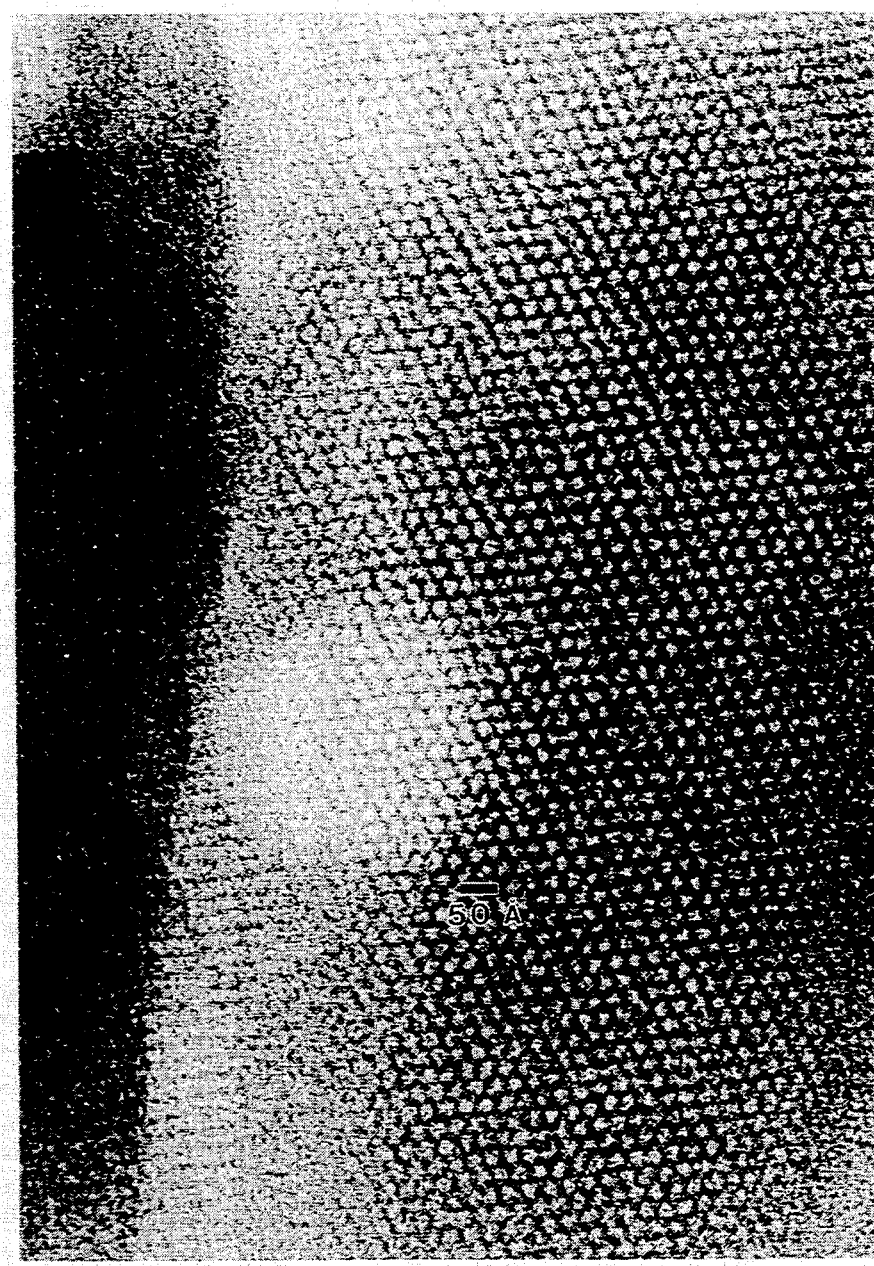
FIG. 20 is a transmission electron micrograph of the product of Example 5.

FIG. 20 is an electron micrograph from a microtomed thin section of the crystalline product from Example 5. This micrograph shows a reasonably regular array of somewhat smaller channels in a hexagonal arrangement. The repeat distance between the channels is about 30 Angstrom units, which is consistent with the position of the first peak in the X-ray diffraction pattern (25 Angstroms/$\sqrt{3}/2$) of this material. The smaller pore size of this material was also verified by Argon physisorption measurements reported in Example 22(a), where a value of 16.9 Angstrom units was calculated for the material in Example 5.

Figure 21:
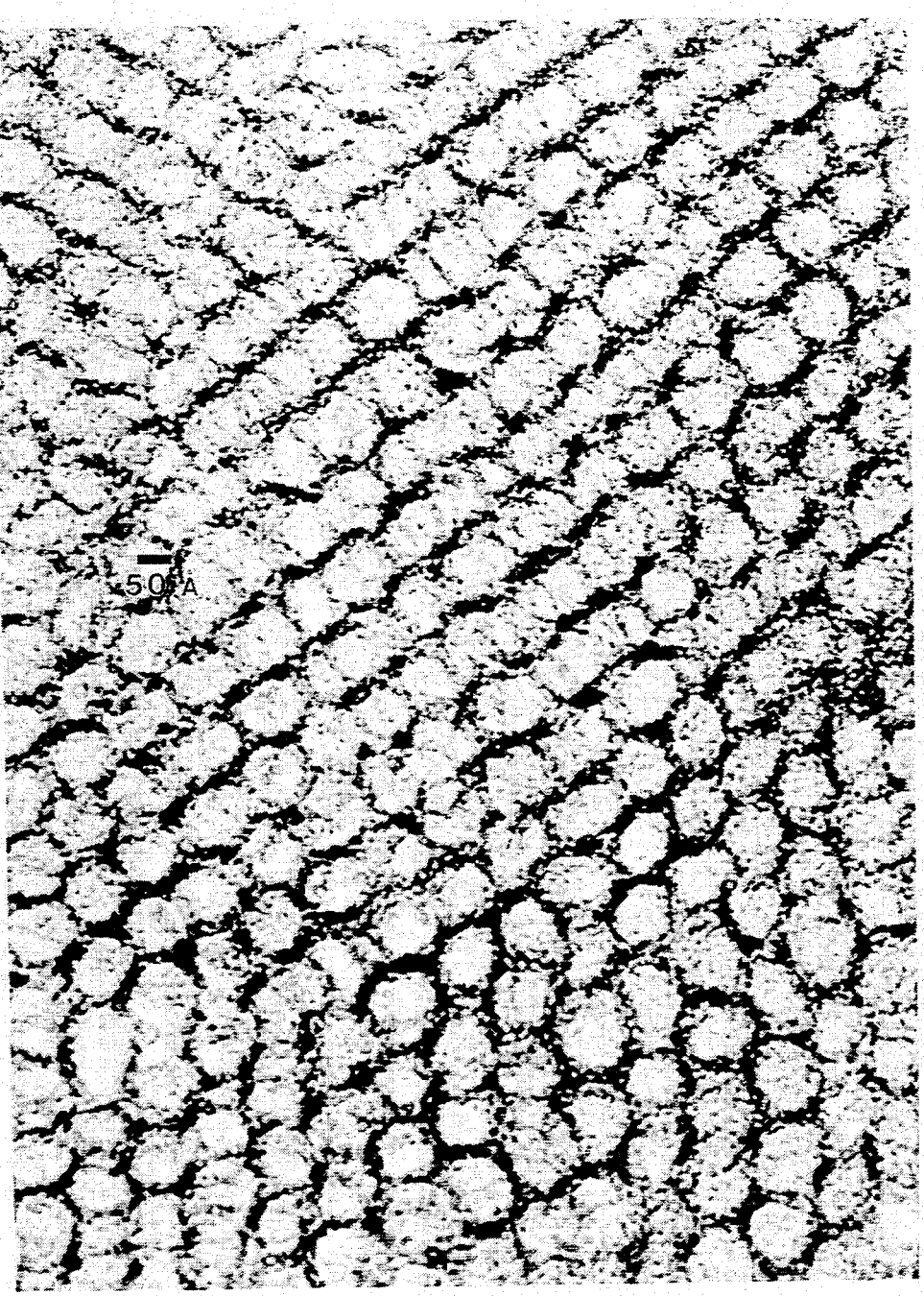
FIG. 21 is a transmission electron micrograph of the product of Example 19.

FIG. 21 is an electron micrograph from a microtomed thin section of the crystalline product from Example 19. The channels in this image are quite large and rather irregular, but the characteristic hexagonal arrangement of the material of the present invention is evident.

EXAMPLE 24

Preparation of Mesoporous Crystalline Material
d(1)=62 Angstroms 1.65 g of Na AlO$_2$ were added to cetyltrimethylammonium hydroxide (CTMAOH). The reactants were stirred vigourously until the NaAlO$_2$ was completely dissolved. To this solution were added 40.0 g of tetramethylammonium silicate (0.5 TMA:1 SiO$_2$, 10 wt % SiO$_2$) and 10.0 g of amorphous precipitated silica (HiSil TM) (90 wt % SiO$_2$). Immediately after this addition, 18.0 g of trimethylbenzene (TMB) was added and the reaction was stirred vigorously for about 10 minutes. The resulting gel was then loaded into a 300ml autoclave and heated rapidly to 105° C. while stirring at 150 rpm. After about 4 hours of heating, the reaction was quenched with ice water, and the contents were removed. The product was filtered and washed several times with warm (60°-70° C.) distilled water and with acetone.

The resulting product was determined to be an inorganic, porous crystalline phase material having, after calcination, a hexagonal arrangement of uniformly-sized pores having diameters of at least about 15 Angstrom Units and exhibiting a hexagonal electron diffraction pattern that can be indexed with a d$_{100}$ value of about 62 Angstrom Units.

EXAMPLE 25

2-Phase Reaction of KI and n-Bromopentane 20.741 g of potassium iodide were dissolved in 16.283 g of water and 7.526 g of 1-bromopentane were subsequently added. The two-phase mixture was stirred vigorously using a magnetic stirrer and heated to 80° C. over a 20 minute period. The reaction mixture was monitored over a subsequent three hour period without a catalyst. Then 1,004 g of the mesoporous crystalline material of Example 24 was added and the reaction continued for 1.75 hours at 80° C. The reaction mixture was then cooled, filtered, and the clear organic phase separated from the aqueous layer. The Table below shows results of gas chromatography analysis at various reaction times.

TABLE

| Reaction Time (hours) | Temp. (.C) | Bromo-pentane (area %) | Iodo-pentane (area %) | Others (area %) | Comments |
|---|---|---|---|---|---|
| 0 | ambient | 98.55 | 1.45 | 0.0 | |
| 0.3 | 80 | 94.18 | 5.82 | 0.0 | |
| 1.3 | 80 | 91.68 | 8.32 | 0.0 | |
| 2.3 | 80 | 76.49 | 23.1 | 0.0 | |
| 3.3 | 80 | 79.44 | 20.56 | 0.0 | Catalyst added after |

TABLE-continued

| Reaction Time (hours) | Temp. (.C) | Bromo-pentane (area %) | Iodo-pentane (area %) | Others (area %) | Comments |
|---|---|---|---|---|---|
| 5.1 | 80 | 8.31 | 86.50 | 5.20 | sample taken Analysis after work-up |

Figure 22:
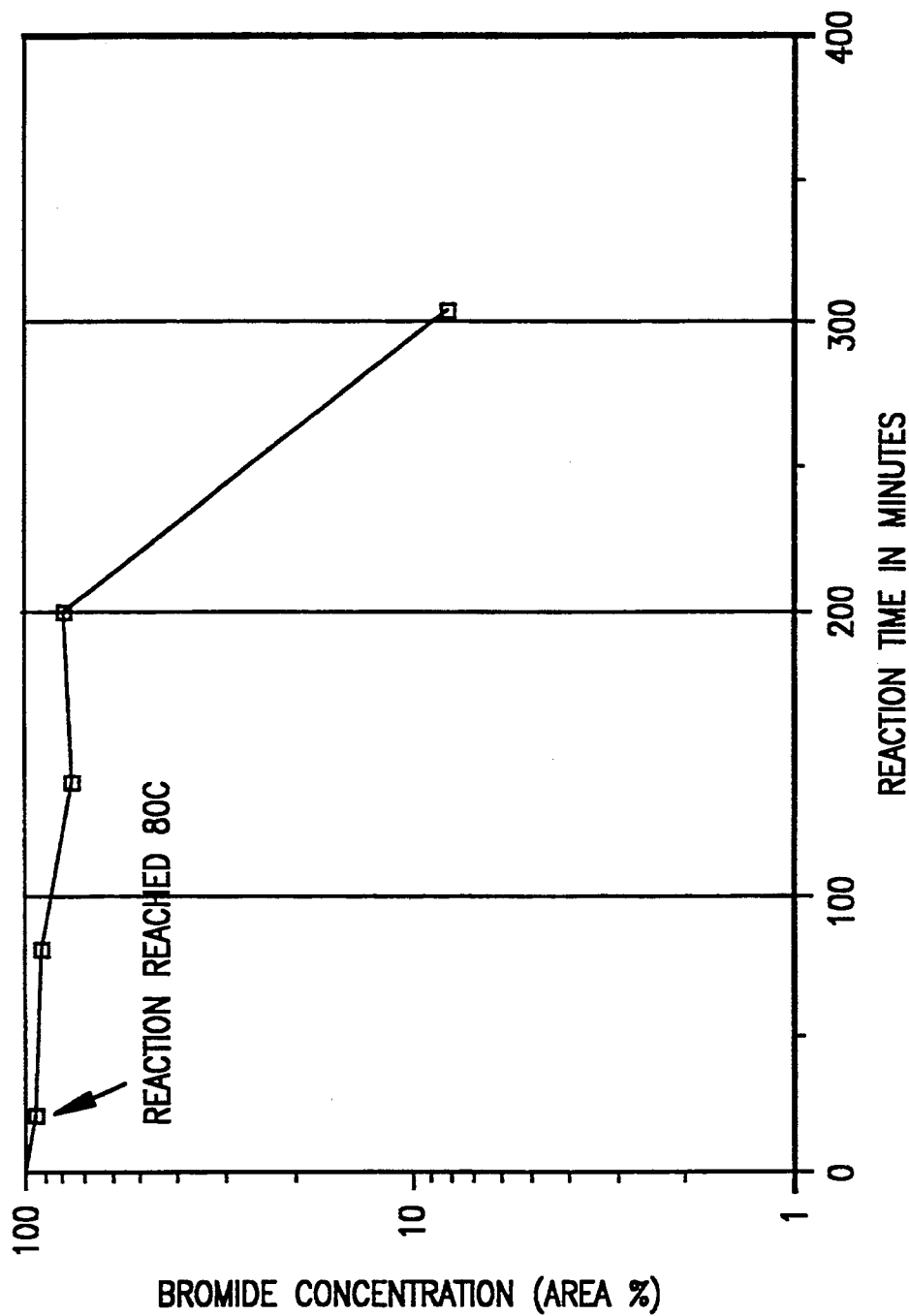
FIG. 22 depicts a log plot of the concentration of bromopentane versus reaction time in the reaction of potassium iodide with bromopentane and shows the rate enhancement attributable to the phase transfer catalysis method of the present invention.

A log plot of the concentration of bromopentane versus reaction time shows the significant rate enhancement caused by addition of the mesoporous crystalline material to the reaction mixture (FIG. 22). This assumes halogen exchange is a first order reaction under these conditions and that the slope of curve is proportional to the rate constant. Therefore, the ratio of the slopes before and after addition of the mesoporous crystalline material is proportional to the catalytic enhancement under these conditions.

What is claimed is:

1. A method for carrying out phase-transfer catalysis in a plural phase reaction system containing an organic phase and an aqueous phase, maintained under phase-transfer catalysis conditions, with a synthetic composition of matter comprising an inorganic ultra-large pore non-layered crystalline material which contains immobilized onium ion within its pores, wherein said crystalline phase material has a hexagonal arrangement of uniformly-sized pores having diameters of at least about 15 Angstrom Units, and a composition, expressed on an anhydrous basis as follows:

$$rRM_{n/q}(W_aX_bY_cZ_dO_h)$$

wherein R is the total organic material not included in M and comprises an onium ion of the formula:

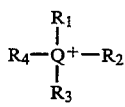

wherein Q is nitrogen or phosphorus and wherein at least one of $R_1$, $R_2$, $R_3$ and $R_4$ is aryl or alkyl of from 6 to about 36 carbon atoms, the remainder of $R_1$, $R_2$, $R_3$ and $R_4$ being selected the group consisting of hydrogen and alkyl of from 1 to 5 carbon atoms; r is the number of moles or mole fraction of R; M is one or more ions; n is the charge of the composition excluding M expressed as oxides; q is the weighted molar average valence of M; n/q is the number of moles or mole fraction of M; W is one or more divalent elements; X is one or more trivalent elements; Y is one or more tetravalent elements; Z is one or more pentavalent elements; a, b, c, and d are mole fractions of W, X, Y, and Z, respectively; h is a number from 1 to 2.5; and ($a+b+c+d$)=1, said crystalline phase exhibiting a hexagonal electron diffraction pattern that can be indexed with a $d_{100}$ value greater than about 18 Angstrom Units whereby said composition of matter transfers a functional reactant ion or group from one phase to another phase.

2. The method of claim 1 wherein the sum ($a+b+c$) is greater than d, and $h=2$.

3. The method of claim 1 wherein W comprises a divalent first row transition metal or magnesium; X comprises aluminum, boron, gallium or iron; Y comprises silicon or germanium; and Z comprises phosphorus.

4. The method of claim 1 wherein W comprises cobalt, X comprises aluminum, Y comprises silicon and Z comprises phosphorus.

5. The method of claim 1 wherein at least one of $R_1$, $R_2$, $R_3$ and $R_4$ is selected from the group consisting of $-C_{10}H_{21}$, $-C_{16}H_{33}$ and $-C_{18}H_{37}$, or combinations thereof.

6. The method of claim 1 wherein said onium compound is selected from cetyltrimethylammonium, cetyltrimethylphosphonium, octadecyltrimethylphosphonium, myristyltrimethylammonium, decyltrimethylammonium, dodecyltrimethylammonium and dimethyldidodecylammonium compounds.

7. The method of claim 1 wherein R comprises an auxiliary organic selected from (1) aromatic hydrocarbons and amines having 5-20 carbon atoms and halogen- and $C_1$-$C_{14}$ alkyl-substituted derivatives thereof, (2) cyclic and polycyclic aliphatic hydrocarbons and amines of 5 to 20 carbon atoms and halogen- and $C_1$-$C_{14}$ alkyl-substituted derivatives thereof and (3) straight and branched chain aliphatic hydrocarbons and amines having 3-16 carbon atoms and halogen-substituted derivatives thereof.

8. The method of claim 7 wherein the auxiliary organic is selected from the group consisting of p-xylene, trimethylbenzene, triethylbenzene, and triisopropylbenzene.

9. The method of claim 1 having original M ions replaced, at least in part, with an ion or a mixture of ions selected from the group consisting of hydrogen and hydrogen precursors, rare earth metals, and metals of Groups IA, IIA, VIIA, VIIIA, IB, IIB, IIIB, IVB and VIIB of the Periodic Table of the Elements.

10. The method of claim 9 wherein said replacing ions comprise hydrogen or a hydrogen precursor.

11. The method of claim 1 wherein said phase transfer catalysis comprises anion exchange.

* * * * *

UNITED STATES PATENT AND TRADEMARK OFFICE
CERTIFICATE OF CORRECTION

PATENT NO. : 5,347,060
DATED : September 13, 1994
INVENTOR(S) : Stuart D. Hellring et al It is certified that error appears in the above-indentified patent and that said Letters Patent is hereby corrected as shown below:

Col. 29, line 24 (claim 1), after "phase" (2nd occurrence), insert --comprising contacting the reactants,--.

Col. 29, line 24 (claim 1), after "maintained" insert --in a liquid phase and--.

Col. 29, line 27 (claim 1), after "crystalline" insert --phase--.

Signed and Sealed this

Eighth Day of November, 1994

Attest:

BRUCE LEHMAN

Attesting Officer     Commissioner of Patents and Trademarks